US007872575B2

(12) United States Patent
Tabe

(10) Patent No.: US 7,872,575 B2
(45) Date of Patent: *Jan. 18, 2011

(54) HOMELAND INTELLIGENCE SYSTEMS TECHNOLOGY "H-LIST"

(76) Inventor: Joseph Akwo Tabe, 11700 Old Columbia Pike, Suite 717, Silver Spring, MD (US) 20904

(\*) Notice: Subject to any disclaimer, the term of this patent is extended or adjusted under 35 U.S.C. 154(b) by 121 days.

This patent is subject to a terminal disclaimer.

(21) Appl. No.: 11/821,776

(22) Filed: Jun. 25, 2007

(65) Prior Publication Data

US 2009/0115603 A1 May 7, 2009

(51) Int. Cl.
    *G08B 21/00* (2006.01)
(52) U.S. Cl. ............ 340/540; 340/541; 340/539.12; 340/539.26; 340/506; 340/511; 340/521; 340/425.5; 128/903; 128/904; 600/300; 600/301
(58) Field of Classification Search ............... 340/540, 340/541, 539.12, 573.1, 632, 506, 511, 521, 340/425.5, 539.26; 128/903, 904; 600/300, 600/301
    See application file for complete search history.

(56) References Cited

U.S. PATENT DOCUMENTS

| 4,827,943 | A  | * | 5/1989  | Bornn et al. ............. 600/481 |
| 5,873,369 | A  | * | 2/1999  | Laniado et al. ........... 600/300 |
| 6,198,394 | B1 | * | 3/2001  | Jacobsen et al. ......... 340/573.1 |
| 6,891,470 | B2 | * | 5/2005  | Bohinc, Jr. ............. 340/539.26 |
| 7,034,677 | B2 | * | 4/2006  | Steinthal et al. ........ 340/539.12 |
| 2007/0146145 | A1 | * | 6/2007  | Lehrman et al. ......... 340/573.1 |
| 2007/0273394 | A1 | * | 11/2007 | Tanner et al. ............ 324/664 |
| 2007/0297569 | A1 | * | 12/2007 | Saunders ................. 378/108 |

\* cited by examiner

*Primary Examiner*—Tai T Nguyen

(57) ABSTRACT

Homeland Intelligence Systems Technology "H-LIST" comprises nano-sensors embedded in a silicon substrate and etched/fused in a micro-fibered material. The silicon substrate is alloyed with miniaturized steel responsive to weapons, preventing bullet penetration and providing effective detection platform on an outfit. The outfit is operable for monitoring suspicious terrorist activities and for tracking biological and chemical gases, and explosives, including weapons of mass destruction and physiological conditions of personnel. Disclosed embodiments provide wearable detection apparatus comprising plurality sensors on an outfit configured to be worn by military personnel, an officer, a security officer, a bus driver, hostesses, Doctors, civil establishment hospital patients and the like, for protection and for sensing deadly gases, explosives, and physiological conditions in a defined area. A receptor is operatively configured and worn proximate to the outfit responsive detection signals. The receptor is communicatively connected to the sensors and operable for receiving/analyzing detection signal communications wirelessly indicative of the presence of a sensed agent, whereby detected signals are transported wirelessly to a central security monitoring station, providing communications to first responders. The communications could be reachable to backup security personnel or agents, prompting them to respond to the vicinity of the detection. The sensors are multifunctional and coded to recognize wavelike pattern of gases and explosives traveling through the wave. Embodiments provide the outfit and the receptor being operable to process the portion of the detection signal to determine the detection type and/or whether there is a concealed object by conducting a test in which a first characteristic of a first dielectric constant associated with a person is determined, and a second characteristic of a second dielectric constant associated with the concealed object and or weapons of mass destruction is determined to expedite data transmission and communication to first responders.

49 Claims, 18 Drawing Sheets

FIG. 7   DETECTION ARRAY

FIG. 8    RECEPTOR PRIVACY INDICATOR

WIND TOWER ON A MILITARY SHIP

FIG. 10  VARIOUS NETWORKS

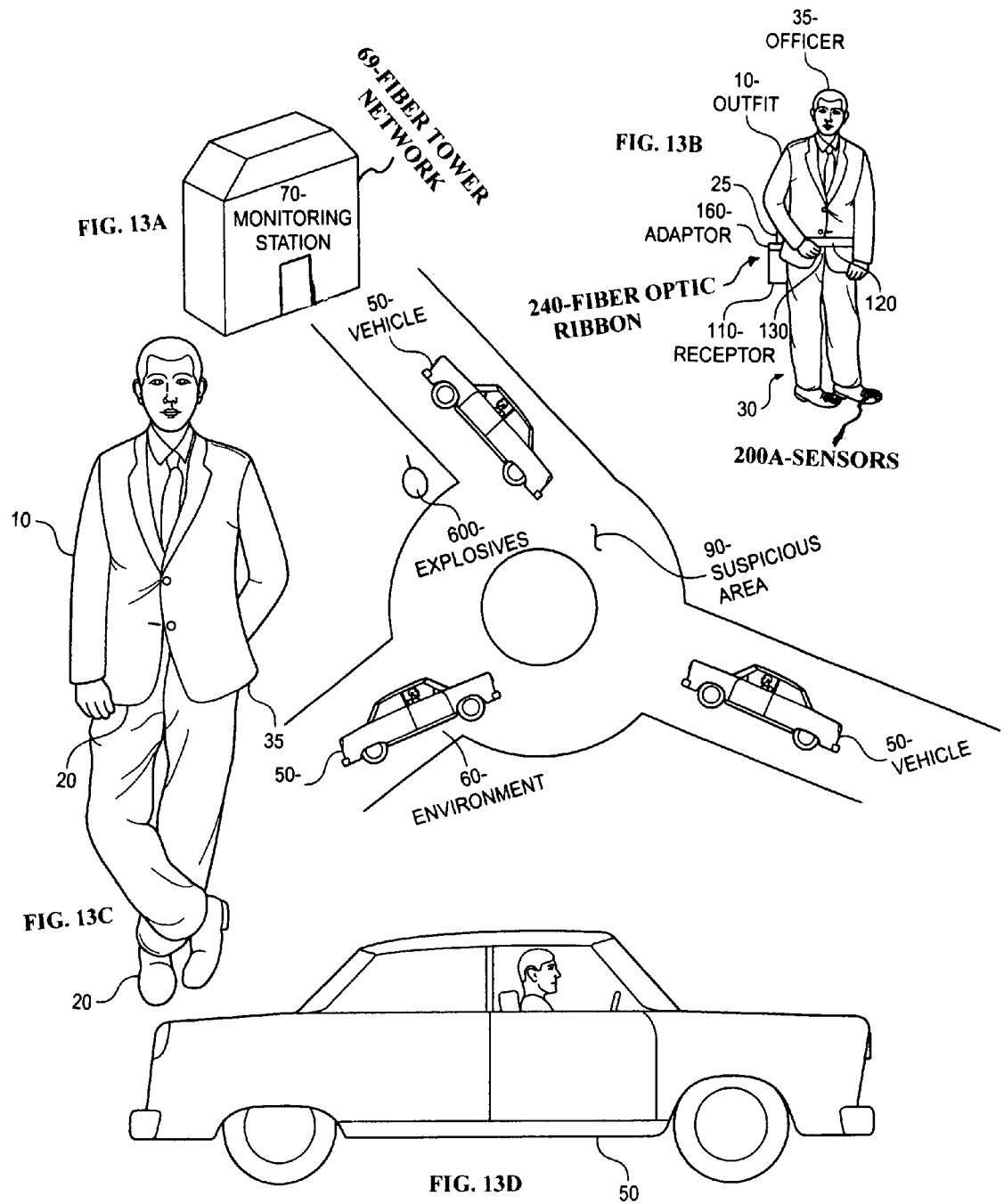

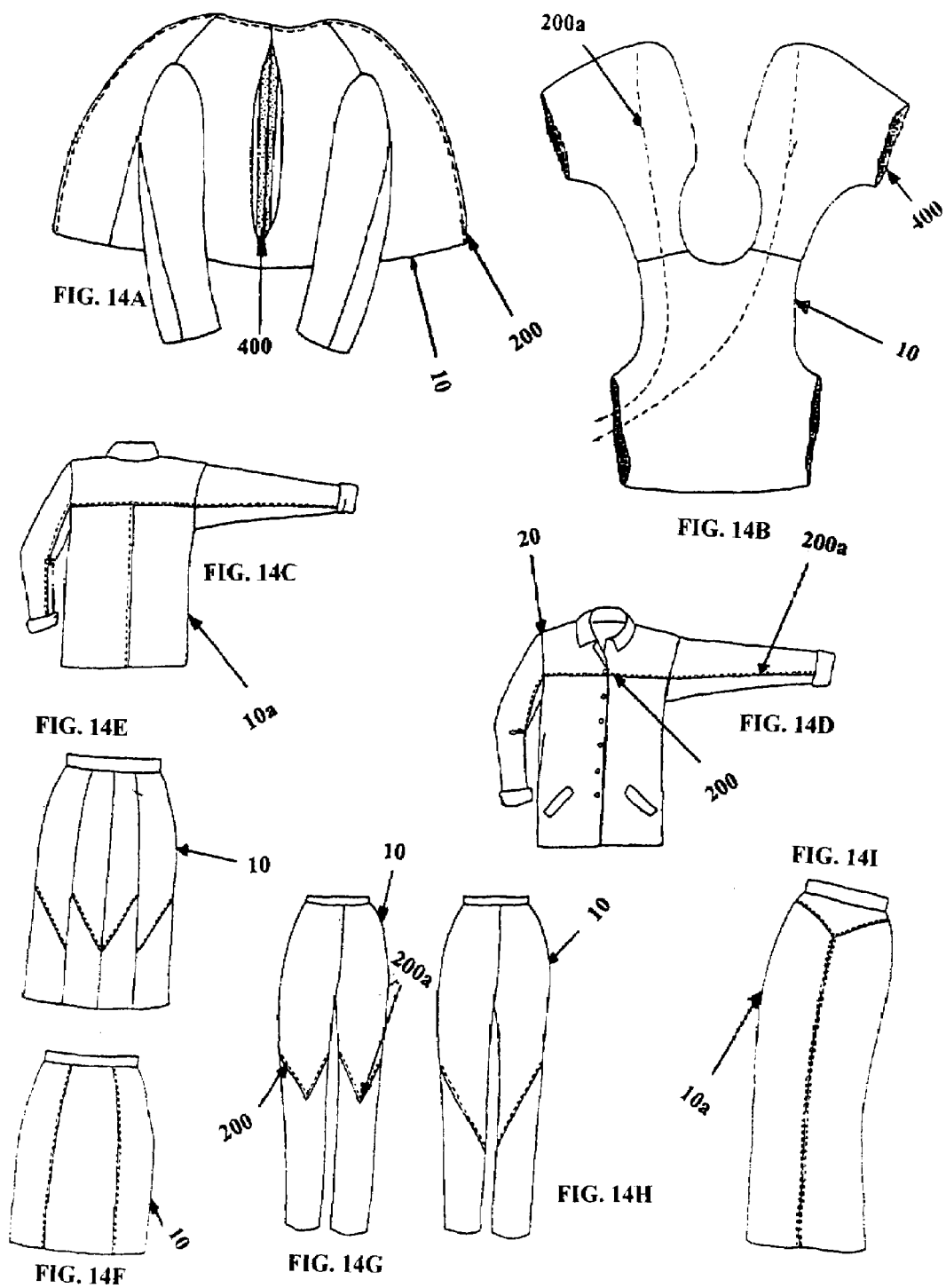
FIG. 14 DIFFERENT COMBINATIONS OF OUTFIT DESIGNS

HOMELAND INTELLIGENCE SYSTEMS TECHNOLOGY "H-LIST"

This application claims benefit from a Provisional Application Ser. No. 60/426,800, filed Nov. 18, 2002, U.S. application Ser. No. 10/660,473, filed Sep. 12, 2003 and now U.S. Pat. No. 7,271,720 issued Sep. 18, 2007. All of these applications are incorporated by reference herein in their entirety.

PURPOSE

Disclosed embodiments provide wearable approach to enable mobile detection and monitoring. Terrorist activities today are so globalized and positioning that stationary devices can not keep up with the mobility. Embodiments provide advanced global positioning against terrorist activities and is operable to reveal a mobile and innovative approach to home-land intelligence. Disclosed embodiments is configured to:

1. Provide digital combat on a battlefield.
2. Provide home-land intelligence
3. Advance homeland security technology into randomly patrolled mobile system.
4. Keep airport perimeters and access under secured security control system.
5. Safeguard personnel against bacteria caused by the launching of weapons of mass destruction.
6. Provide revolutionary advanced wearable detection device for civil establishment hospital patients and Doctors.
7. Reduce the hassles involved in airport securities and procedures while also improving and safeguarding the lives of occupants.
8. Monitor battlefield personnel physiological signs, their heart rates, and their respiratory system.
9. Monitor battlefield enemies, their movements, and the location of their weapons.
10. Provide wireless digital network for home-land environment, homeland security and army personnel.
11. Advance technologies that will provide flight attendants with self protection for the safety of aircrafts and their occupants.
12. Improve homeland security standard when defending an assigned area of a building.
13. Improve security standards on transit trains, trucks, buses and the like.
14. Besides barriers or security guards, drivers will safeguard their buses against explosives, chemical or biological agents, and drugs such as narcotics.
15. Nuclear power plants access restriction will be better safeguarded.
16. Improve security standards on power plants such as nuclear power plant and the like.
17. Provide innovative military advanced combat gears.
18. Provide detection of weapons of mass destruction or when a chemical or biological gas has been used in a battlefield and ensure a timely evacuation of the area so affected.
19. Provide detection of anthrax spore, bacterial, fungal spores, and viruses.

FIELD OF THE INVENTION

Embodiments provide Home-Land Intelligence Systems Technology comprises a revolutionary multipurpose nanotechnology application on a detection platform for a wearable outfit operable for detection, protection, and monitoring of and intervention into monitored environments. Disclosed embodiments consist of nano-sensors embedded in silicon substrate and etched/fused in a micro-fibered material with excellent electrical characteristics to exhibit effective and efficient detection platform on the outfit responsive to various national emergency conditions. Certain embodiments of the disclosure provide a receptor operatively configured for analyzing detection data in communication with the detection platform. Disclosed embodiments provide the receptor being worn proximately close to the outfit and communicatively configured for providing direct communication to a central communication post when detection is enabled. Disclosed embodiment further provide wearable apparatus operable with higher sensitivity and selectivity of current and projected forms of detection of and protection against weapons of mass destruction. Some embodiments provide wearable apparatus for monitoring, and protection against biological and chemical contexts. Certain embodiments provide wearable apparatus configured for facilitating the hyper-sensitive and selective monitoring and control of assigned environments. Disclosed embodiments provide the wearable apparatus comprising outfit that protects the body against body bacteria from weapons of mass destruction. Certain embodiments provide a wearable apparatus that monitors battlefield personnel physiological signs, their heart rates, and their respiratory system. Other embodiments of the disclosure provide the wearable apparatus being configured with the receptor being operable to report all communicative data and detected information to the central security reporting stations or network. Some embodiments provide the stations comprising a network being operable with interactive links in communication with the receptor and other law enforcement networks to enable instant response to anticipatory attack.

Disclosed embodiments further provide nanotechnology based outfit being configured for detection and communication. Certain embodiments provide a revolutionary multipurpose wearable outfit application through a detection platform configured for detection, protection, and monitoring of personnel physiological conditions in a hostile environment. The wearable outfit consists of nano-sensors embedded in silicon substrate. Some embodiments provide the silicon substrate being etched/fused in a micro-fibered material having excellent electrical characteristics to provide effective and efficient detection platform being operable for monitoring the physiological conditions, including heart rate, vital signs, and blood pressure. The detection platform further provides detection of the environmental conditions at the vicinity of personnel assignments. Embodiments provide the receptor in communication with the detection platform for analyzing detection data about the personnel's physiological condition and for providing direct communication to a central communication post. The sensitivity and selectivity of detection characteristics are important, thus, embodiments provide current and projected forms of detection of and protection against environment conditions associated with influencing a change in physiological conditions.

BACKGROUND OF THE INVENTION

Prior art teachings of biological, chemical, and explosive detection devices have been developed and mounted on fixed positions to perform assigned tasks, such as locating explosive devices through sensors at the gateway of airports, or doorway of government buildings. Still, some undetected explosives have been used to blow off planes and buses because some how, the prior art devices failed to detect the explosives at the time they were unwrapped from their carefully sealed plastics. Other detection devices are so disturbing when used within portable environment, including around the airport and government buildings operable to detect weapons of mass destruction on ones body. More so, terrorist groups are expanding the act of suicide bombing through technologies, which are strategically planned for and carried on the public streets, public transportations, recreational environments, or outside some government buildings. With the suicide bomber's strategic selection of key targets and location to perform such deadly acts, current detection systems have no way of sensing that a parked car with explosives and the like, is in front of any of these locations waiting to be detonated.

Disclosed embodiments provide materials, sensors being configured on a wearable platform in communication with a communication apparatus for processing detection data of personnel's physiological conditions. Certain embodiments provide the detection data being analyzed and networked as conceptualized within the homeland security. Some embodiments provide the communication apparatus being operable through control functions in communication with the detection platform. Disclosed embodiments provide the communication apparatus comprising a receptor configuration, being operable to provide real time communication. Certain embodiments provide the detection platform comprising wearable outfit operable for outfitting personnel so that a consistent network to physiological detection and communication is ascertained, including individual activities of the personnel, which may require them to plug-in their bodies into hostile environment. Disclosed embodiments further provide the communication apparatus being operable for communicating not only the detection data, but also any detected body information and behaviors of personnel being monitored according to their medical emergence.

Prior art devices for homeland security detection thrive upon the formation of different devices such as stationary detection devices. These stationary devices are nowhere more apparent than emergent nanotechnologies with embedded nano-sensors approach for providing detection of personnel physiological conditions. Disclosed embodiments provide silicon-micro-fiber approaches to nanotechnology applications in homeland intelligence as the future of invasive technological approach to detection, protection, and monitoring of, and the intervention of threat to personnel. Certain embodiments of the disclosure provide a wearable detection platform configured with threat functions for applications in any environment in which failure to detect could lead to a dominant disaster in that nation, the military, and the civil medical environment.

Some prior art devices focuses only on signal interception, but have no way of detecting explosives that are in a parked car, or on the body of a person entering a bus. Other prior art devices have failed to detect explosives on the body of a person who carefully sealed such device and successfully finds his way inside an air plane. Yet, prior art devices have failed to detect explosives already used within an environment and contain deadly gases. Moreover, some deadly gas applications on a battle field are not visible after being lunched, including a chemical or biological weapon. Prior art devices would not detect explosive that has successfully gotten inside a stadium on a super bowl game and just waiting to be detonated. Disclosed embodiments provide detection method that advances the intelligence of homeland security. Certain embodiments of the disclosure provide a portable detection apparatus that provide mobile detection of explosives and deadly gases in a person's body, or inside a parked car on the street. Applicant acknowledges that besides fixed or stationed detection machines, homeland security can intelligently be operable to protect its environment if the detection devices are mobile, have wireless means to communicate, and can be self carried by security officers.

Applicant also acknowledges that for the detection device to be self carried and used intelligently, it has to be worn by the security officers at the vicinity of the protective area. Disclosed embodiments provide a wearable detection apparatus comprising an outfit configured for security officers. With disclosed embodiments, a security officer is sure to patrol an assigned area randomly with the device in his body and alarming thereof if a weapon is detected. Certain embodiments provide advanced methods of approaching homeland security and the monitoring of our nation. Disclosed embodiments provide biosensors comprising chemical sensors with high selectivity and sensitivity. Some embodiments provide the biosensors comprising of (a) biologically active material. Certain embodiments provide an oscillating piezoelectric crystal in conjunction with nano-sensors being embedded in a detection platform configured for an outfit operable for detections. The detection platform is configured to detect an environment which is affected by the change in mass being sensed on the surface of the crystal due to the resonant frequency on the sensing materials. Some embodiment provide the sensing material being made of non-ferrous material such as silver and or gold to provide ideal biosensor layer for detection of any liquid, solid. Disclosed embodiments provide gaseous phase explosive detection being operable in their mobile environment. The change in mass occurs when the frequency changes as a result of the environmental condition. The change in mass is measured by a piezoelectric immunosensors in communication with a receptor.

The potential application of this technology includes civil establishment hospitals, law enforcement agencies, industrial applications, security agencies, Homeland security, Military, postal services, transportation and transit authorities, airports and aviation environment. Certain embodiments provide a revolutionary approach to detections, comprises nanotechnology applications consisting of nano-sensors being configured for bringing signals that contain chemical targets into contact with the detection platform, allowing chemical targets to be bound to discrete region of the various sensor means.

The receptor is operable for eying these biochemical sensors, comprises analytical tool that consists of biologically active materials such as surface resonance spectroscope communication with devices disclosed embodiments being operable to convert biochemical signal into quantifiable electrical signal. Disclosed embodiments further provide devices being operable for communication. Certain embodiments provide a communication apparatus being operable for communicating detected information. Detection is being provided through the electrical signals or pulses. These electrical signals or pulses are signal communications traveling between the detection platform and the receptor. The detection signals are transported wirelessly through waves, including radio waves and/or microwaves, to the central security monitoring stations. Prior art devices are not wearable, and disclosed embodiment is a wearable outfit that include camouflage outfit configured with sensors for detection of weapons of mass destructions. Furthermore, prior art devices are limited in their zones and have no way of extending sensitivity to detecting explosives in a parked car. Disclosed embodiments provide a detection platform on a wearable outfit configured for protective sensing, and is not limited to analytical techniques of detecting, polluting, water and microbial contamination analyses, industrial gases and liquids, mining and toxic gases, explosives and military arena; but extends to protecting the airports, transport planes, government buildings, tunnels, city malls, recreational areas, battle field personnel, common buildings and the like. Certain embodiments provide biochemical sensor, including at least one of:

(a) A receptor: responsible for the selectivity/sensitivity of a sensor to transform chemical or biological information into energy form which is measured by a transducer. The receptor part is based on physical, chemical, or biochemical principles and functions like an analyzer, sampling responses and transporting said responses through processed signals as a function of time, e.g. enzymes, antibodies, and liquid layers.

(b) A detector: like a transducer, responsible for translating the physical or chemical change by recognizing the analyte and relaying it through electrical signals to a receptor, e.g. pH can be a pH-electrode, an oxygen electrode, or a piezoelectric crystal to measure the target analyte without using reagents.

(c) Transducer: responsible for transforming chemical or biological energy into useful analytical signal.

(d) Electrochemical sensor: responsible for transforming the effect of the electrochemical interaction analyte electrode into useful signal.

(e) Electrical chemical sensor: responsible for measuring the change in electrical properties caused by the interaction of the analyte.

(f) Thermometric chemical sensors: responsible for measuring the heat effects of a specific chemical reaction or absorption which is involved in an analyte (g) Optical chemical sensor: responsible for transforming changes of optical phenomena as a result of an interaction of the analyte with the receptor part.

(h) Magnetic chemical sensors: responsible for the change of paramagnetic properties of the gas being analyzed.

(i) Mass sensitive sensor: responsible for transforming the mass change at a specially modified surface into a change of a property of the support material. The mass change is caused by absorption of mass of the analyte at the oscillator.

(j) Photo-ionization detector: detects unknown organic gases and vapors and also determines their concentration level.

(k) APD 2000: detects the presence and relative concentrations of military chemical agents, e.g. sarin, mustard gases, cesium (l) Bioassay strips: determines the presence of some biological agents and send results to an optical reader in the receptor to evaluate the test strip.

(m) RFID chip, a nano-structured processor for detection of weapons of mass destruction, detection of functional inability of personnel, and also for wirelessly networking with stations or fiber towers.

Applicant acknowledges that the design of the detection platform within the outfit may include at least one of the five design techniques:

1 Piezoelectric thin film coating through pattern recognition technique.
2 Cantilever beam deflection technique.
3 Piezoelectric AlN Thin films sensors
4 Infrared reflectometry technique
5 Micro electro-mechanical system with RFID chip.

The advancement of the detection outfit in H-LIST provide biological sensing elements which would selectively recognize a particular biological molecule through a reaction specific adsorption, or other physical or chemical processes. The detection platform is configured for allowing the transducers to convert the result of its recognition into a usable signal, which can be quantified and amplified. Disclosed embodiments provide a transducer operable for detection analysis consist of at least one of optical, electro-optical, or electrochemical devices configured for plurality sensing opportunities. Some embodiments provide biosensors operable for specific applications such as Homeland Intelligence Systems Technology "H-LIST." A typical detector such as a transducer will translate physical or chemical change within an area by recognizing an analyte and relaying its analysis through signal communication from the wired/wireless connections with the embedded sensors disposed in the detection platform. The detection platform is in signal communication with the receptor in communication with centralized stations.

Disclosed embodiments further provide apparatus for processing biological or chemical gases, and involves binding of chemical species with another chemical species, which has a complementary structure. H-LIST provide two classes that have the bio-recognition processes for detection. These classes are bio-affinity recognition and bio-metabolic recognition and offer different methods of detection. Bio-affinity recognition has stronger binding and enables the transducer to detect the presence of the bound receptor-analyte pair and provide communication thereof. However, with the receptor-ligand and antibody-antigen bind, the processes are common to the detection environment.

Disclosed embodiments further provide detection apparatus comprising of pattern recognition technique and operable for different recognition, such as metabolic recognition, where the analyte and other co-reactants are chemically altered to form the product molecules and providing communication thereof. The biomaterials that can be recognized by the bio-recognition elements are as varied as the different reactants that occur in biological system's detection in which analyte molecule will have a complementary structure to the antibody while the bound pair will be in a lower energy state than the two separate molecules, making it very difficult to break. Disclosed embodiments provide interaction between antibodies with corresponding antigen, including an antibody based chemical and biosensors like immunosensors. When antibody is raised against an analyte, an immunosensors would enable its recognition. The specificity and affinity of antibodies towards complementary ligand molecules would prevent most antibody antigen interactions from causing any electronically measurable change. However, a piezoelectric effect in various crystalline substances would allow detection of analyte within that vicinity.

Disclosed embodiments provide Piezoelectric immunosensors operable to detect antigens both in gaseous phase and liquid phase. Certain embodiments provide Piezoelectric being operable to detect micro-bacteria antigen in biological fluids and is incorporated in the design of H-LIST, a wearable and portable device for providing detection of gases and explosives in any environment. Devices to detect weapons of mass destruction have been previously used in the art but all failed to teach a portable and wireless system with sensors wired in an outfit for detection and communication. Example of such device is described in U.S. Pat. No. 4,866,439 and discloses an explosive detection system for aircrafts to deter terrorist activities. This system fails to show a portable and mobile system needed for homeland security. U.S. Pat. No. 5,465,607 teaches an explosive detection screening system for detection of explosives and other controlled substances. This system shows detection of relatively volatile and non-volatile vapors and particulates but did not teach a wired outfit detection device. U.S. Pat. No. 3,718,918 teaches detection of nuclear explosion through radiated transient radio frequency signal and still fails in its teaching to show a wired outfit system that enables communication to at least a network when detection is eminent.

U.S. Pat. No. 6,573,107 teaches immunochemical detection of explosive substance in the gas phase through surface plasmon resonance spectroscopy. Still, the system fails to teach a portable, mobile and communicative system wired in an outfit to enable network interface. U.S. Pat. No. 6,569,630 teaches a method and composition for aptamers against anthrax. This system relates to detection of biological agents using different compositions and still fails in its entirety to teach a wired outfit for biological and chemical agent detection in their mobile environment. All the above references cited, whether taken in singularly or in any combination, failed to teach a wired outfit design for detection of weapons of mass destruction in anticipation of terrorism.

SUMMARY OF THE INVENTION

Disclosed embodiments provide a wearable detector crystal in alpha quartz, which is suitable for piezoelectric applications in the silicon-micro-fibered material comprising embedded sensors for detections. The crystal in alpha quartz is insoluble in water and have better resistance to high temperatures and electrical properties. Disclosed embodiments provide apparatus operable for the transformation of electronic detection system in homeland security. The resonant frequency of the quartz crystal depends on the physical dimension of the quartz plate and the thickness of the electrode deposited. These crystals are in the form of a disc, square, or rectangle in their design. The piezoelectric quartz crystal is driven by a low frequency transistor oscillator in the receptor and is powered by a direct current regulator power supply. Certain embodiments provide the crystal being mounted on a holder with a stainless steel with leads embedded inside the silicon and etched on the micro-fibered material. The receptor oscillator circuit is configured with frequency counter connected to the oscillator device of the receptor. Some embodiments provide silver composite communicatively connected to the electrode, enabling the crystal electrodes to be modified with a 5 ml coating of protein A, and providing better adhesion of the antibodies to the surface of the transducer. Embodiments provide Protein A, which is a polypeptide isolated from staphylococcus aurues to bind specifically to the immunoglobulin molecules for sensor sensitivity and selectivity for trained specific recognition.

Furthermore, Homeland security involves some personnel casting their bodies in environments that require invasive monitoring. These environments are sometimes affected with chemical and/or biological agents and sometimes are exposed to temperature conditions that are harmful to the personnel and can limit their focus and concentrations. Disclosed embodiments provide methods to improve vast information network for personnel who throw their bodies on hostile environments. Certain embodiments provide wearable apparatus to monitor personnel's physiological conditions and provide direct communication to a command/communication post.

The incorporation of silicon substrate in the configuration of a detection platform would enable the outfit to exhibit some contraction and expansion at key sections of the body, while the electrical characteristics of the micro-fibered material would advance detection sensitivity and selectivity. The detection platform would comprise of the silicon substrate, the micro-fibered material, and plurality nano-sensors each configured for specific detection, such that the physiological condition of personnel are monitored and various detection data are communicated to the command/communication post.

Disclosed embodiments provide wearable outfit configured with contracting characteristics at key points of the body. Certain embodiments provide apparatus configured to reveal data about the personnel assigned in hostile environments. Additionally, if the personnel's condition was initiated by a fall in which broken body parts were detected, the outfit would serve as the first initial treatment to the broken body parts while also providing communication to a command/communication post. In the environment where weapon of mass destruction has been detected, the outfit would serve as a protective gear and a monitoring device. Disclosed embodiments provide a detection apparatus operable with GPS configured for directing responders to the vicinity of the detection, providing first hand information and the conditions of the environment and also the conditions of each personnel. Medical preparation for personnel's physiological conditions would be accelerated with the the first hand information. In addition, some treatments would be readily administered through the outfit configuration. The sensors are being coated with silicon substrate polymer and/or with zinc oxide layer to provide energy transport platform.

Disclosed embodiments provide silicon substrates consisting of at least one of: polydimethylsiloxane, amorphous silica, petroleum distillates, methyltriacetoxy silane, ethyltriacetoxy silane for the detection platform.

Certain embodiments provide apparatus for monitoring personnel's physiological conditions, and for protecting the personnel's body from getting in contact with external exposure to emergency environmental conditions. In this regard, the outfit would further serve as a sealant that would resist environmental conditions, including severe weather conditions, and would exhibit flexibility, toughness, and also served as a body waterproof.

Applicant acknowledges that different techniques may be employed in transforming biochemical sensors, such as infrared reflectometry to characterize the thickness. Certain embodiments provide optical properties of thin films being operable for the advancement of the integrated circuit for converting solar energy into electrical energy. Disclosed embodiments further provide smaller feature sizes, faster switching speeds, and lower power consumption. Some embodiments provide basic wiring such as dielectric and photolithographic layers, providing a circuit for electrical energy production. This integrated circuit could employ copper/low-k interconnects, silicon-germanium and silicon on insulator-based transistor structures, or chemically amplified deep ultraviolet and x-ray lithography and new metal silicide ohmic contact materials. Infrared spectroscopy offers a metrology approach to sensing through the outfit, complementary to UV-VIS techniques that provide excellent sensitivity to layer composition, including chemical bond densities and free carriers with the enhanced immunity to roughness induced scattering. Infrared spectroscopy shares many of the inherent advantages of UV-VIS spectroscopy as a non-destructive process control tool for further usage in H-LIST because it can be implemented as a reflectance sensor embedded within the outfit. A reflectance spectrum is acquired by incorporating a reflectometer equipped with a linearized liquid nitrogen detector. Software is also incorporated to analyze input to the model-based.

The dielectric function of the layer is modeled with a set of damped harmonic oscillators closely spaced in frequency, with equal damping constants and spacing. The arrays of oscillators are located in the spectral regions where absorption is expected in the film. During the fit, the amplitudes of the oscillators, high frequency dielectric constant, and layer thickness are varied to fit the model to the measured data. By combining model-based infrared spectral analysis with high performance reflectometry hardware, disclosed embodiments would extract quantitative data on multiple parameters relating to film properties. Disclosed embodiments further provide unique sensitivity to film composition, which is applicable to a wide range of films including ultrathin oxides, doped semiconductors, and complex materials such as photoresists and low-k dielectrics. Certain embodiments provide high accuracy reflectometer which characterizes the reflectance of ultrathin gate oxides and chemically amplified deep ultraviolet photoresist thin films configured to further convert solar energy into electrical energy. The gate oxide reflectance data is related to the deposition time needed to model the thermal oxidation growth kinetics. Disclosed embodiments employ non-destructive measurements on every product wafer as a means of gathering data and information needed to control the process of monitoring biological or chemical gases or weapons of mass destruction in a confined environment. Some embodiments provide ultraviolet visible reflectometry and ellipsometry relating to electromagnetic radiation of wavelengths beyond the violet end of the visible light spectrum method for production monitoring of transparent thin films.

BRIEF DESCRIPTION OF THE DRAWINGS

In order that the invention may be readily carried into effect, it will now be described with reference to the accompanying drawings, wherein:

FIG. 1 is seen to represent a piezoelectric quartz and receptor transducer on a detection platform outfit connected to a receptor.

FIG. 3 is seen to represent a cantilever beam system on a detection platform connected to a receptor.

FIG. 13 is seen to represent security officers with their outfit worn and monitoring a street and the government building on the said street.

FIG. 14 is seen to represent the different possible combinations of outfit design for monitoring means.

DETAILED DESCRIPTION OF THE INVENTION

Figure 2:
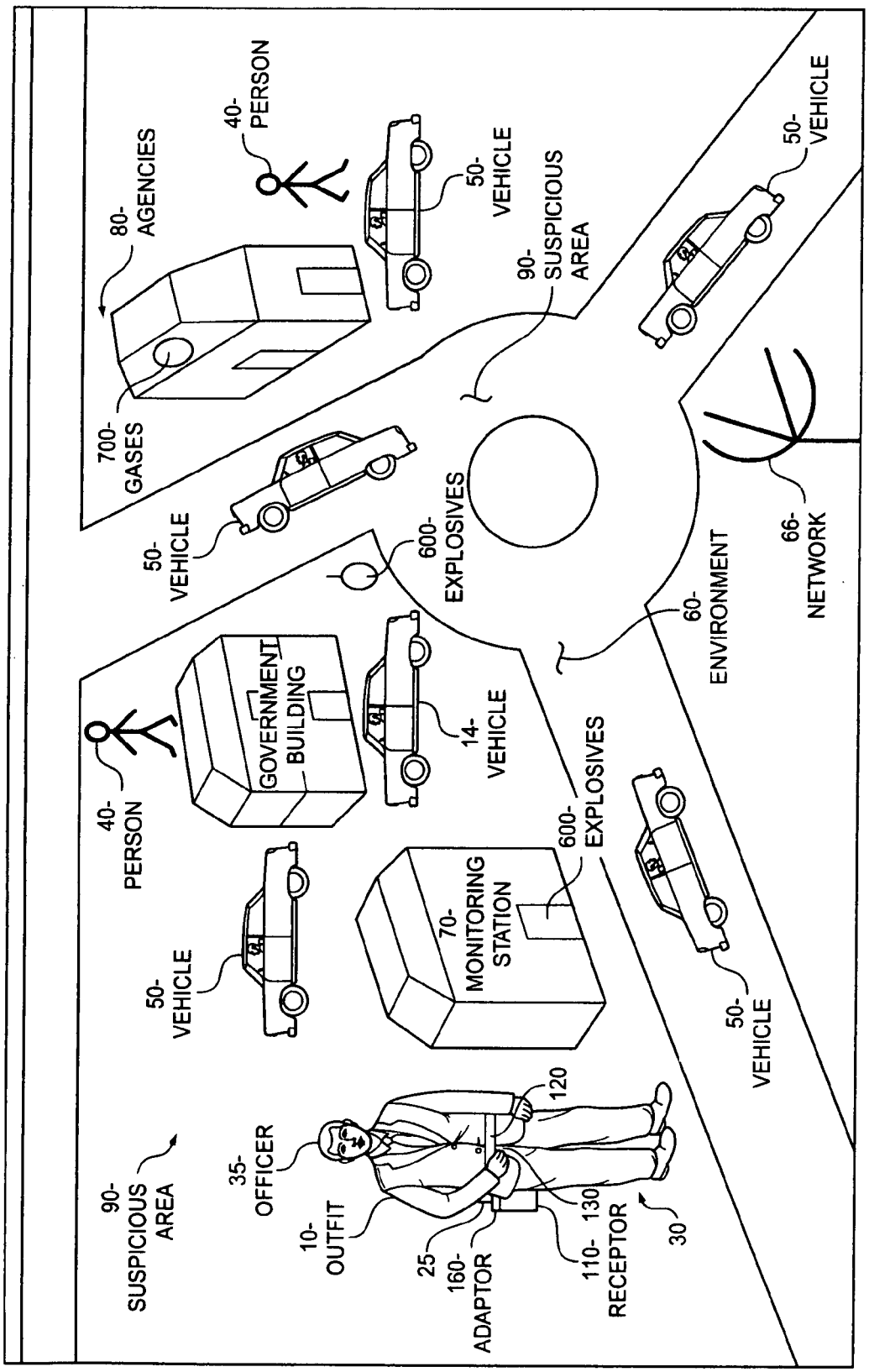
FIG. 2 is seen to represent an officer randomly patrolling an environment.

The terminology used herein is for the purpose of describing particular embodiments only and is not intended to be limiting of embodiments. As used herein, the singular forms "a", "an", "at least", "each", "one of", and "the" are intended to include the plural forms as well, unless the context clearly indicates otherwise. It would be further understood that the terms "include", "includes" and/or "including", where used in this specification, specify the presence of stated features, integers, steps, operations, elements, and/or components, but do not preclude the presence or addition of one or more other features, integers, steps, operations, elements, components, and/or groups thereof. In describing example embodiments as illustrated in the drawings, specific terminology is employed for the sake of clarity. However, the disclosure of this patent specification is not intended to be limited to the specific terminology so selected and it is to be understood that each specific element includes all technical equivalents that operate and/or function in a similar manner. It would be further noted that some embodiments of the enclosed communication apparatus is used concomitantly and/or not used concomitantly with megatel. In some embodiments, the communication apparatus comprises a platform array responsive to media communications. In some embodiments, the communication apparatus further comprises of a platform array responsive to signal radiation. Other embodiments herein describe apparatus configured for entertainment.

The foregoing and/or other objects and advantages would appear from the description to follow. Reference is made to the accompanying drawing, which forms a part hereof, and in which is shown by way of illustration specific embodiments in which the embodiments may be practiced. These embodiments being described in sufficient detail to enable those skilled in the art to practice the teachings, and it is to be understood that other embodiments may be utilized and that further structural changes may be made without departing from the scope of the teachings. The detailed description is not to be taken in a limiting capacity, and the scope of the present embodiments is best defined by the appended claims. Referencing the drawings, wherein reference numerals designate identical or corresponding parts throughout the several views, exemplary embodiments of the present patent application are hereafter described. The numbers refer to elements of some embodiments of the disclosure throughout. As used herein, the terms "and/or" and "at least one of" include any and all combinations of one or more of the associated listed items.

Figure 1:
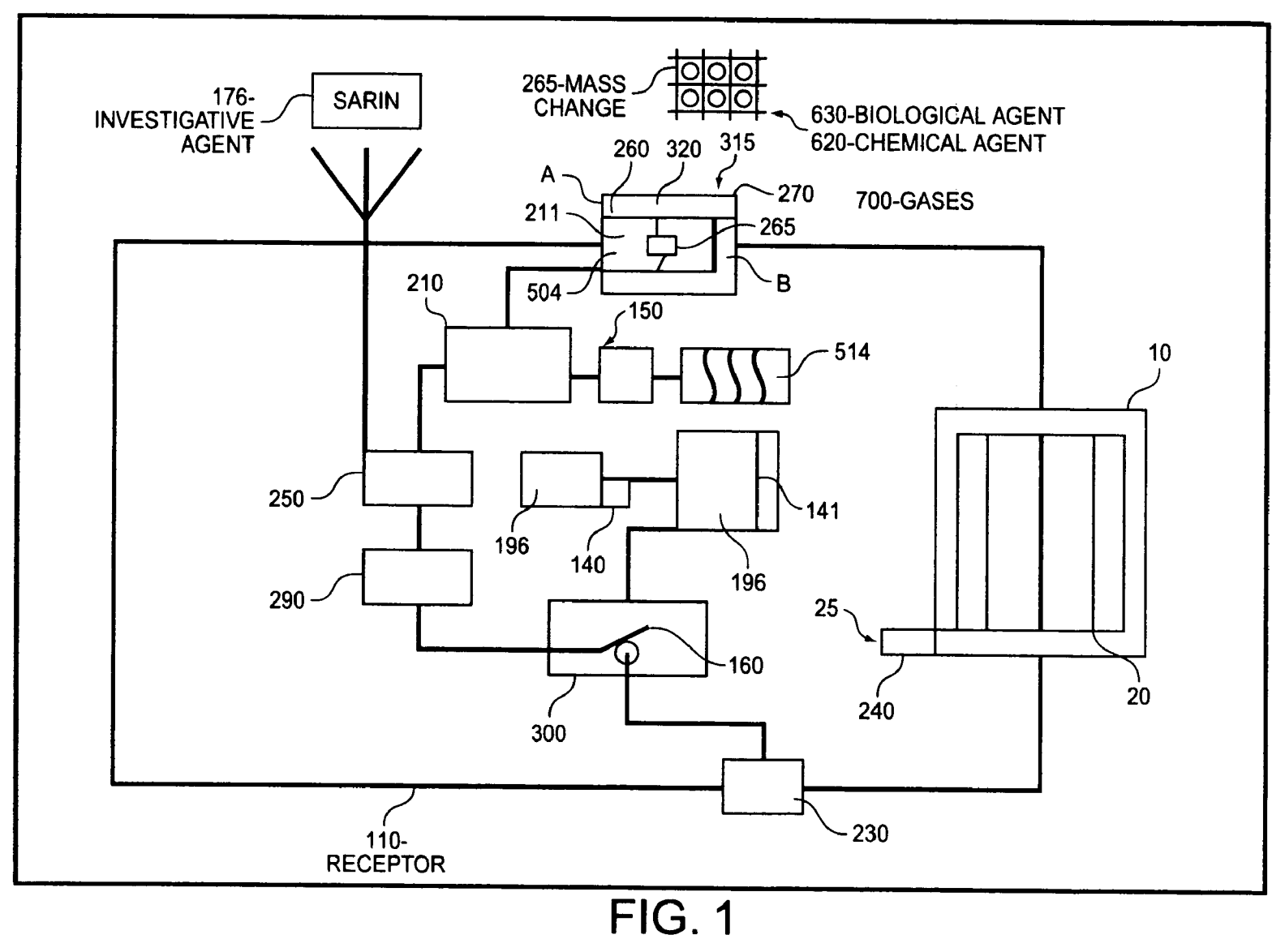

Referring to FIG. 1 is seen nanotechnology applications on an outfit 10 configured with at least a lining 20, a connector 25, and a fiber optic ribbon 240. The outfit 10 is operatively configured with an interface 300 comprising an adaptor 160, an electronic nose 230, and at least a detector 290. Plurality detectors are provided comprising sensitive detector 250, cantilever sensor 210, and piezoelectric detector 211 configured with piezoelectric crystals 260. The detectors are operatively connected to at least a chip 140, in communication with a controller 196 and 320. A CPU 141 is provided responsive to signals from the controllers 196 and 320. An analyzer 150 comprising an analyte is configured to analyze at least a resonance frequency shift 514. The piezoelectric detector 211 comprises piezoelectric crystal 260, being operable to allow antibodies 270 being coated with the crystals to provide multiple use potentials in solid, liquid, gaseous and explosive detections. The antibodies 270 are coated on the surfaces of the piezoelectric to provide a change of mass 265. An investigative agent 176 is configured with at least the analyte responsive to useful signal communications.

Referring to FIG. 2, is seen an environment 60, comprising a monitoring station 70, agencies 80 and a government building. Vehicles 14 and 50 and at least a person 40 are being watched by an Officer 35 monitoring a suspicious area 90. The Officer 35 is outfitted with the embodiments of current invention comprising outfit 10, adaptor 160, receptor 110, wearable outfit 30, waist belt 120, connector 25 being disposed within the waist area 130. Officer 35 is seen to have identified a suspicious person 40 patrolling at least agencies 80. The outfits 10, 30, and 120 are seen to show exemplary embodiments of detected explosives 600 and gases 700. The receptor 110 is seen to have analyzed the detections and is in communication with a network 66.

Figure 3:
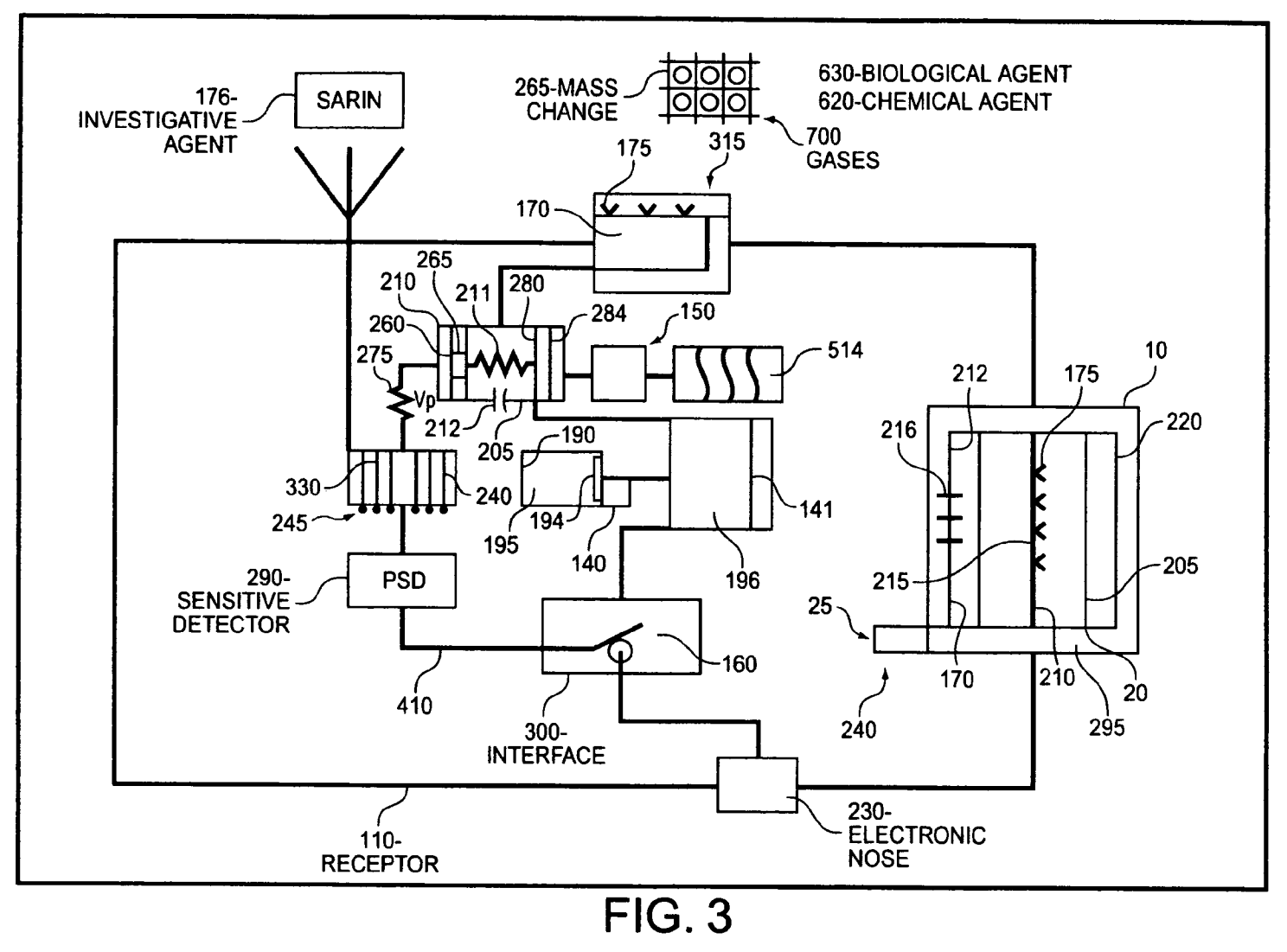

Referring to FIG. 3 is seen sensory layout for an outfit 10 configured with at least a lining 20, a connector 25, and a fiber optic ribbon 240. Outfit 10 is operatively configured with analyzer 150 comprising an analyte being configured to analyze at least a resonance frequency shift 514. Embodiments provide piezoelectric detector 211 comprises piezoelectric crystal 260, operable with antibodies 270 being coated with the crystals to enable multiple use potentials in solid, liquid, gaseous and explosive detections. The antibodies 270 are coated on the surfaces of the piezoelectric to detect a change of mass 265. An investigative agent 176 is configured with at least the analyte responsive to useful signal communications. The outfit 10 comprises nanotechnology applications comprising nano-sensors 200, 210, 211, 280, 290, and 315. The nano-sensors 200, 210, 211, 280, 290, 315 are embedded in a silicon substrate 205 and etched/fused in a microfiber material 220 to provide more sensitive detection platform 295. The microfiber material 220 comprises of a micro fibered material with excellent electrical characteristics.

Sensor 315 could be a transducer being operatively configured with the detection platform 295 for providing multiple sensing to specific detections. The detection platform 295 further comprises electronic nose 230, responsive to detection of odors. The detection platform 295 is further configured to recognize wavelike properties, such as could be seen in explosives 600, gases 700, biological agents 630, and chemical agent 620. These detections are analyzed by analyzer 150 communicatively configured with investigative agent 176. The investigative agent 176 is operatively configured with the receptor 110 responsible for providing communications indicative of the detection type and communicable to at least a monitoring station 70 and/or at least a network 66 as seen in FIG. 2. Receptor 110 may comprise of at least a GPS technology responsive to identifying personnel locations.

At least a cantilever sensor 210 is further provided and being coated at the side with sensor materials 212 to enable specific detections. Micro machined cavities 216 consisting of multifunctional sensors 215 are further arranged to provide other specific detection types. Detection signals are analyzed as they are exposed to an analyte 175 comprising aqueous solutions. The electronic nose 230 provide detection of odors in communication with at least a receptor layer 170. The receptor layer 170 is communicatively connected to the analyte 175. Receptor 110 further configured with at least an analyte chamber 195 comprising sensor array 330 communicatively connected to input adaptor 160 to provide better detection selectivity and sensitivity. Grains of membranes 190 are etched in the analyte chamber 195 to provide signal separations. Embodiments provide apparatus to read signal simultaneously through beam deflection 284, and the signal may be transmitted through a fiber-optic ribbon 240. Transmission control 194 is configured with receptor 110 responsible for providing information about detected agent, and is responsive to false signals. Signals may be transmitted to transmitter 311, and receiver 312.

The detection platform 295 further comprises microelectronic circuit 410 comprising multifunctional sensor arrays 330, 420, 420. Sensors 290 and 200 are further configured to enable communications through active interface 300. Multiple light sources 245 are operatively connected to membrane 190 and to the analyte chamber 195 responsive to cantilever illumination. Multiple light sources 245 is deflected from cantilever 210 to shine on sensitive detector 250 being responsive to bending due to voltage pressure (Vp). The bending is initiated by photocurrent 275 due to stress. The detector platform 295 is further operatively connected to at least a chip 140, in communication with a controller 196 and 320. A CPU 141 is provided responsive to signals from the controllers 196 and 320. The analyzer 150 comprises an analyte configured to analyze at least a resonance frequency shift 514. The piezoelectric detector 211 comprises piezoelectric crystal 260, which allows antibodies 270 to be coated with the crystals to provide multiple use potentials in solid, liquid, gaseous and explosive detections. The antibodies 270 are coated on the surfaces of the piezoelectric to enable a change of mass 265. An investigative agent 176 is configured with at least the analyte responsive to useful signal communications.

Figure 4:
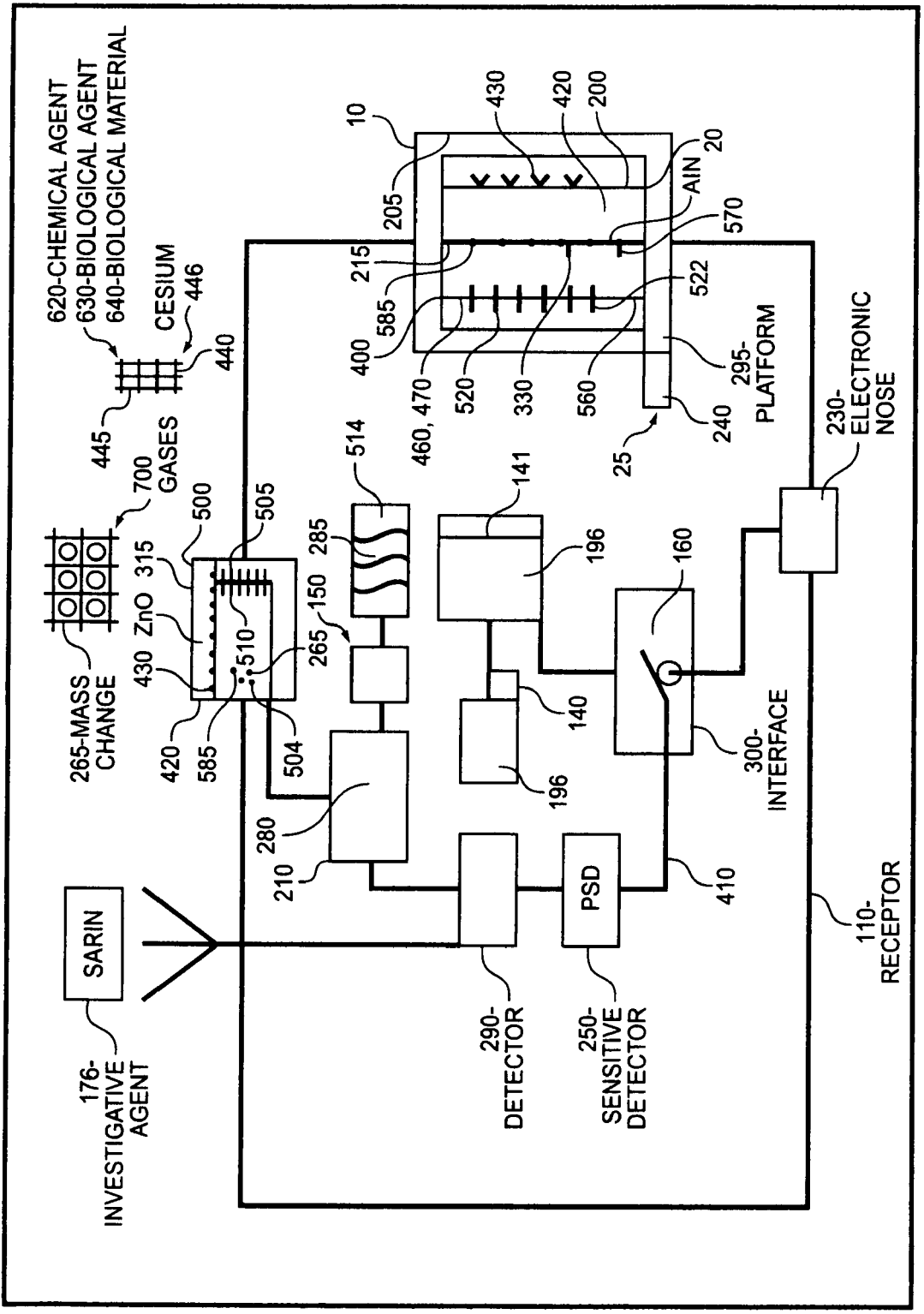
FIG. 4 is seen to represent a piezoelectric and micro electro-mechanical system on a detection platform operatively connected to a receptor.

Referring to FIG. 4 is seen further embodiment of the sensory platform, an outfit 10 is seen comprising at least a silicon substrate 205. The silicon substrate 205 comprises of nanotechnology applications consisting of sensors 200, 215, 280, 330, 400, 420, 430, and AlN. The outfit 10 further comprises of lining 20 responsive to body protection. A ribbon 25 is communicatively connected to an adaptor 160 configured with the outfit 10. Surface acoustic wave line 570 is coated with paste and/or ink 585 comprising of passive glass film. MEMS 420 and multifunctional sensor 215 are configured with a 430, in communication with at least a microelectronic circuit 410 to further convert solar energy into electrical energy. The surface acoustic wave line 570, the paste 585, the MEMS 420, the thin film 430, and the multifunctional sensor array 330 are embedded in the silicon substrate 205 and etched/fused in a micro-fibered material 220 to provide energy generating detection platform 295. The silicon substrate is micro-machined in a chemical and/or electromechanical etch technique.

In other embodiment, a silicon to silicon bonding 460 and/or silicon to ceramic wafer bonding 470 is employed for detection and for generating electrical energy. The silicon to ceramic wafer is further responsive to solar energy. The silicon to ceramic wafer bonding may include at least silicon to glass bonding 470, forming single crystal silicon to improve the micro-acoustics and micro optics in the nanotechnology applications. Multifunctional sensor 215 further comprises surface acoustic wave resonators 500 responsive to frequency shift. The frequency shift may be influenced by mechanical, chemical, and electrical perturbation within the boundary of active interface 300. The electrical perturbations may occur in metal films 543. The metal film 543 may have different conductive values deposited on the resonators 500 responsive to loading effects on the liquid and/or solid media 505. The metal film is further configured for generating electrical energy. Gas selectivity is further influenced by metal clusters 520. The metal clusters 520 are further configured to increase sensor selectivity caused by gas absorption due to the coupling between sensing surface 400 and catalytic properties 504. The catalytic properties 504 consist of metal oxide 530 being further configured for converting pressure force into electrical energy. The metal clusters 520 are operatively configured with sensors 180, 200 to increase selectivity. The metal clusters 520 further comprises semiconductor oxide substrate 560 configured with chemical sensitization to enable metal particles 522 to act as centers for surface gas absorption. The addition of clusters 520 further provide electronic sensitization resulting from oxide surface 540. Disclosed embodiments further provide silicon-substrate-metal oxide 530, further comprising antimicrobial metal consisting of at least silver being laminated to at least a liquid absorbing nonwoven material being fused/etched in microfiber material to provide a pathogen detection environment on the detection platform 295. Certain embodiments provide the silicon-substrate-metal oxide-micro fiber 530 further comprising the nonwoven material consisting of metal coating including metal particles facing at least a liquid absorbing material to retain disinfection effect. Certain embodiments provide wearable outfit comprising sensors 200 being configured to retain antimicrobial effect. Some embodiments provide silicon-substrate-metal oxide 530 being configured with silicon-substrate-thin film 430, providing a detection platform 295 configured with plurality sensors 200 operable for detecting pre-use and post-use of weapons of mass destructions. Certain embodiments provide the nonwoven material comprising at least a polyethylene mesh forming an antimicrobial composites comprising antimicrobial metal coating.

Other embodiment of the of the disclosure provide sensor 315 operatively configured with the detection platform 295 to provide multiple sensing for specific detections. The detection platform 295 further comprises electronic nose 230, responsive to detection of odors. The detection platform 295 is configured to recognize pre-used and post-used of weapons of mass destructions, including wavelike properties, such as could be seen in explosives 600, gases 700, biological agents 630, and chemical agent 620. The detection platform 295 comprises plurality sensors 200, include antimicrobial metal consisting of at least silver being laminated to the micro fiber material 220, including at least a liquid absorbing nonwoven material further comprising perforated firm and a mesh being fused/etched in the microfiber material to provide a pathogen detection environment, and further consist of biomaterial 640 comprising a space charge region 445 operatively configured for surface oxide conductivity 440 within a surface environment 446 operable for converting pressure force, vibration, heat, and sound wave into electrical energy. Disclosed embodiments further provide apparatus for analyzing detections, including an analyzer 150 communicatively configured with investigative agent 176. The nonwoven material is further disposed on the detection platform via vapor deposition. The detection platform further comprises antimicrobial composite comprising liquid permeable material and/or liquid absorbing material operable for pathogen detection. The investigative agent 176 is operatively configured with the receptor 110 responsible for providing communications indicative of the detection type and communicable to at least a monitoring station 70 and/or at least a network 66 as seen in FIG. 2. Receptor 110 and the detection platform 295 may comprise of at least a GPS technology responsive to identifying personnel locations.

The outfit 10 is operatively configured with an interface 300 comprising an adaptor 160, an electronic nose 230, and at least a detector 290. Plurality detectors are further provided, comprising transducers 315 sensitive detector 250, cantilever sensor 210. The detectors are operatively connected to at least a chip 140, in communication with a controller 196. A CPU 141 is provided responsive to signals from the controller 196. An analyzer 150 comprising an analyte is configured to analyze at least a resonance frequency shift 514. The detectors further comprises of antibodies 270 coated with crystals to enable multiple use potentials in solid, liquid, gaseous and explosive detections. The antibodies 270 are coated on the surfaces of the detectors to enable detection of a change of mass 265 within an environment. An investigative agent 176 is being configured with at least the analyte 150 responsive to useful signal communications, including pre-use and post-used of weapons of mass destrsuctions.

Figure 5:
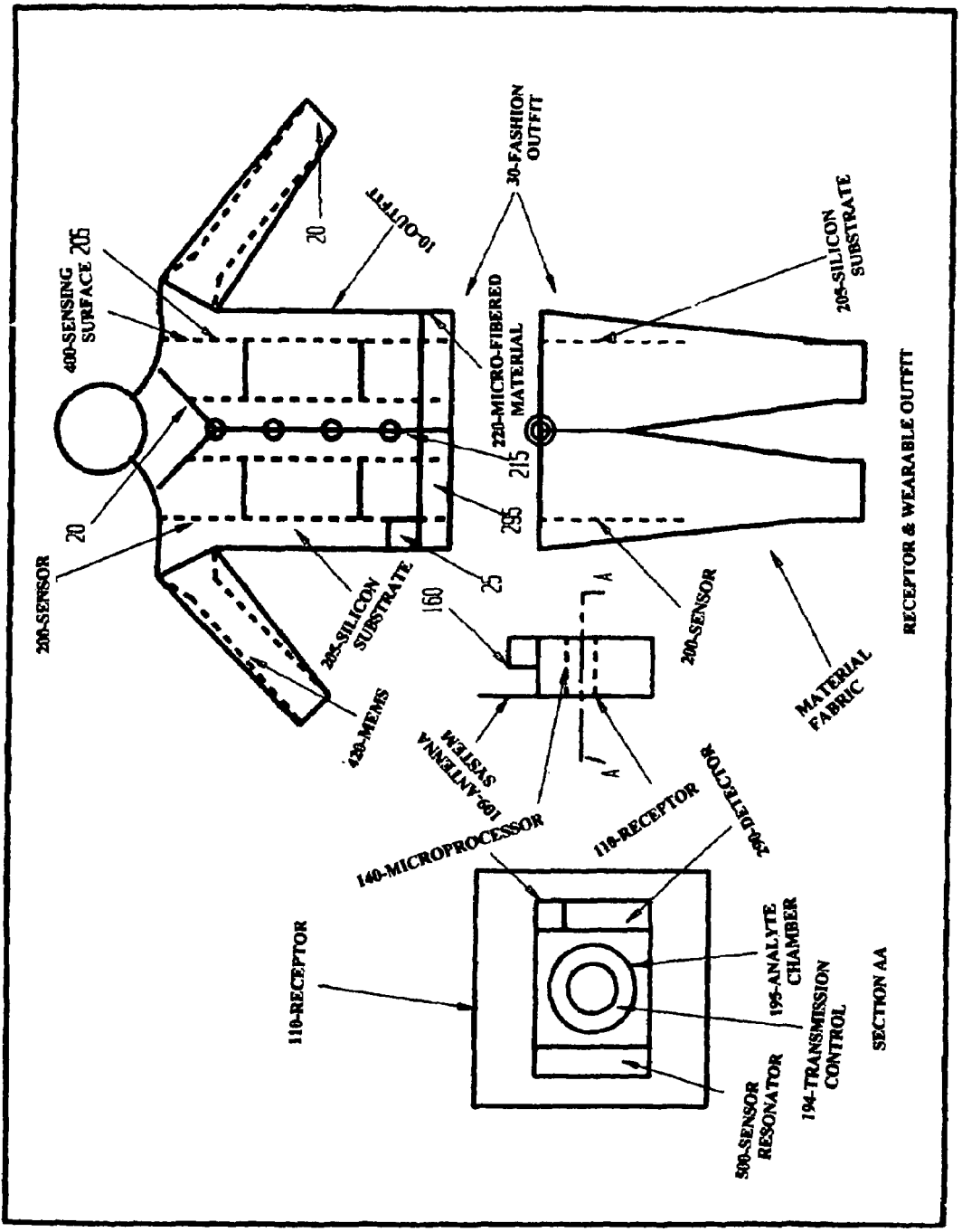
FIG. 5 is seen to represent a receptor and a wearable detection outfit. Section AA is a cutout view of the receptor.

Referring to FIG. 5, at least an exemplary embodiment of outfit 10 comprising a silicon substrate 205. At least a sensor 200 is embedded in the silicon substrate 205 and fused/etched in a micro-fibered material 220 comprising a detection platform 295. The outfit 10 further comprises at least a fashion outfit 30 comprising of at least a material fabric consisting of at least a lining 20 and at least a connector 25 each operatively configured with the detector platform 295. The detection platform comprises at least a sensing surface 400 operatively connected to at least sensors 200 and 420. The lining 20 is responsive to protection. The detection platform 295 is operatively configured with a receptor 110. The receptor 110 comprises at least an adaptor 160 operatively configured with the adaptor for the outfit 10. Section AA is seen to represent sections of the receptor 110 consisting of sensor resonator 500, a transmission control 194, an analyte chamber 195, detectors 290, and a microprocessor 140. The receptor 110 further comprises an antenna 109 responsive to input and output signals. The antenna 109 is operable to increase signal strength and may comprise internal antenna apparatus being configured with a chip operable on a logic circuit. The chip is operatively configured to boost communication signals through the antenna to improve sound quality and reduce dropped communications. The chip is operable on a logic circuit being communicatively connected with the receptor circuit board and in communication with the antenna. Disclosed embodiments provide software in communication with the logic circuit being configured for analyzing signal strength and data speed. The amplification of the signals would improve wireless data transmissions, data card "IC card and SIM card" reception, providing faster data transfer speeds. The chip is further operable to move the wireless signal radiation away from personnel's head and to reduce exposure to cellular radio signals, which may cause health issues. {PRIVATE "TYPE=PICT:ALT=data card signal improvement"} The chip is a solution which depends on antenna configuration and may be operable on CDMA, TDMB, Digital/Analog/GSM, and location area network.

Figure 6:
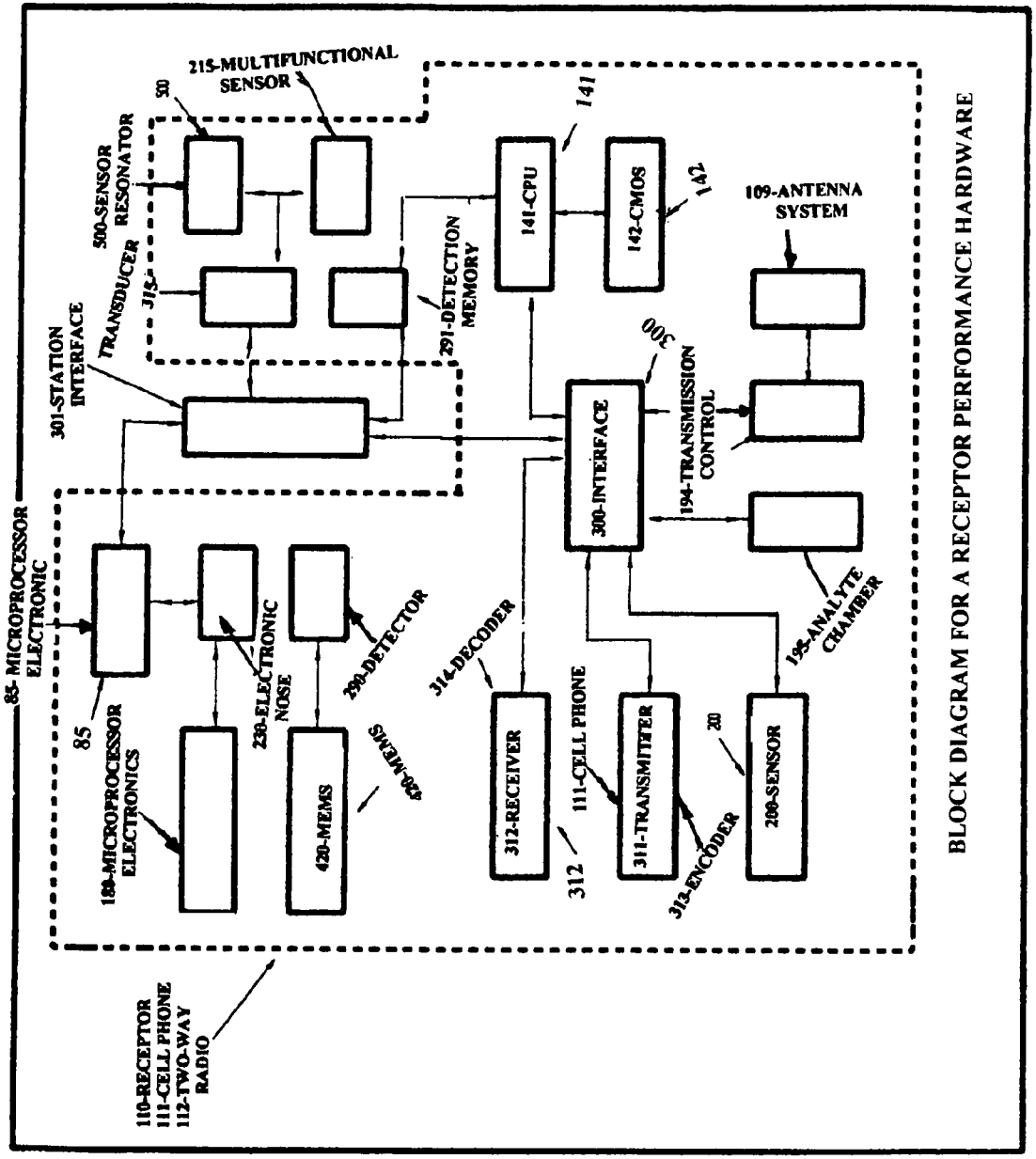
FIG. 6 is seen to represent a block diagram of key components of receptor performance hardware.

Referring to FIG. 6 is seen a block diagram of comprising an exemplary embodiment a receptor 110. Receptor 110 may comprise other communication devices such as at least a cell phone 111, and/or at least a two-way radio. The receptor 110 further comprises of other components, including microprocessor electronics 85 and 180. At least a station interface 301 is operatively configured with the microprocessor electronics 85 and 180. At least a transducer 315 is operatively configured with sensor resonator 500 and multifunctional sensor 215 and communicatively connected to detection memory 291. The detection memory 291 is communicatively connected to station interface 301 and operatively configured with CPU 141. The CPU 141 and the CMOS 142 are communicatively connected to interface 300 comprising at least an analyte chamber 195, at least a transmission control 194, and at least an antenna system 109. Receiver 312, transmitter 311, encoder 313 and decoder 314 are communicatively connected to interface 300. The microprocessor electronics 85 and 180 are communicatively connected to MEMS 420, electronic nose 230, and detector 290. Station interface 301 is operatively configured with interface 300. The receptor 110 further comprises communication control device comprising silicon controlled rectifier consisting of a p-type and n-type gates. The communication control device is further operable in forward and/or reverse bias mode. The silicon control rectifier is further operatively configured for signal amplification and/or communication signal booster. Disclosed embodiments further provide the chip comprising a CMOS 142 operable on a digital circuitry. Certain embodiments provide integrated circuits (chips). The CMOS circuitry is operable to dissipate less power. Certain embodiments of the disclosure further provide a static logic configuration being operable on p-type and n-type metal-oxide-semiconductor field-effect-transistors "MOSFET's." being configured for implementing logic gates. Embodiments provide the CMOS 142 comprising logic being implemented with discrete devices of transistors of both p-type and n-type on a silicon and or silicon substrate 205 commonly called chips, dice, dies. Embodiments provide CMOS 142 comprising fabrication of solar cells on n-type CZ silicon substrates, including Polycrystalline thin-film cells, lightly boron-doped CZ, or gallium-, indium-, and aluminum-doped CZ for converting solar energy, pressure force, sound wave, vibration, wind forge into electrical energy. Disclosed embodiments further provide a thin-film 430 comprising of thin layer of transparent conducting oxide, including tin oxide. Certain embodiments provide the oxides being highly transparent and configured to conduct electricity efficiently. Some embodiments provide antireflection coatings. Other embodiments provide Polycrystalline thin-film cells comprising tiny crystalline grains of semiconductor materials operable for converting solar energy into electrical energy.

Figure 7:
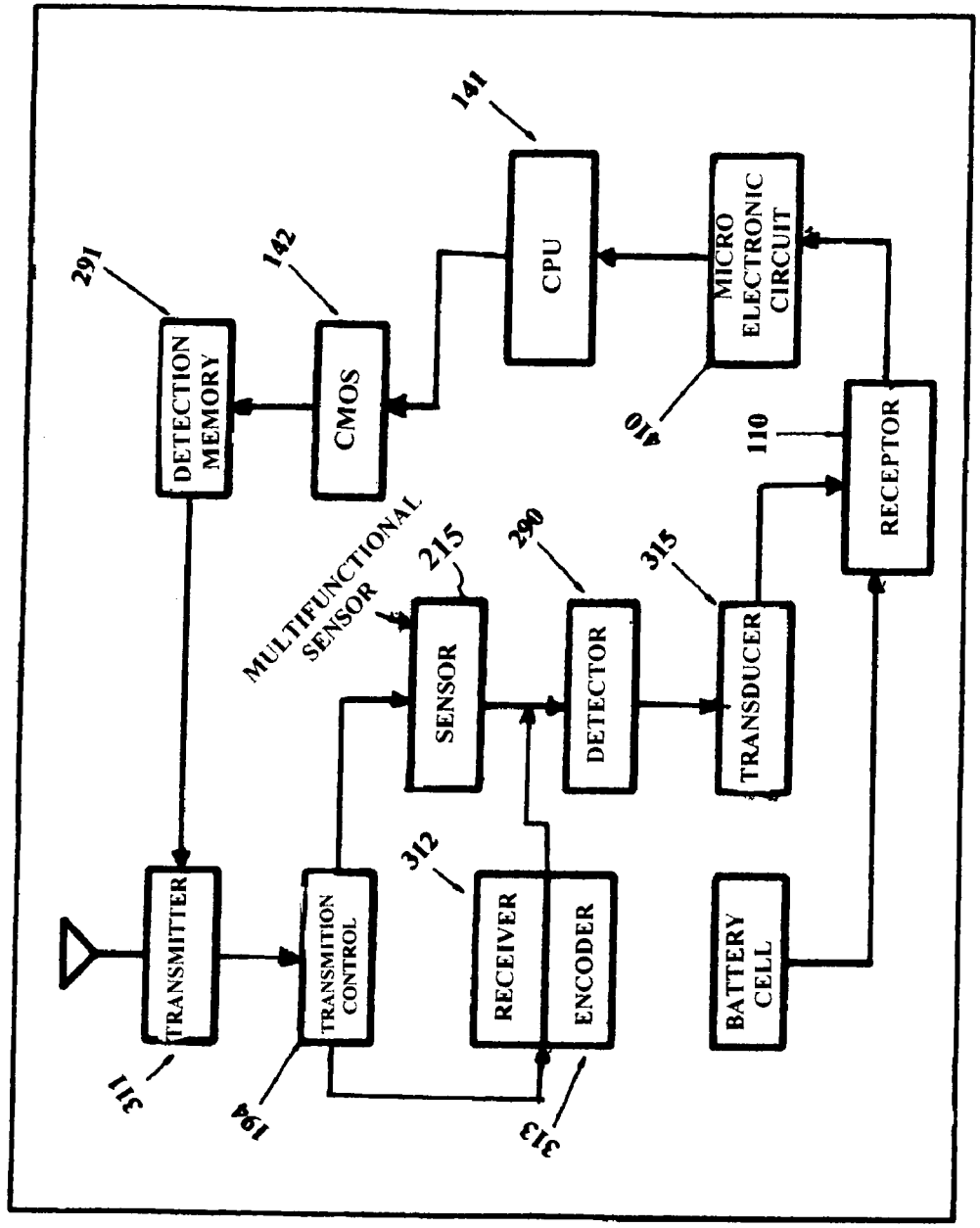
FIG. 7 is seen to represent a detection array of the detection system.

Referring to FIG. 7, a detection array is presented in accordance with other aspects of the disclosure. At least a receptor 110 normally comprise of a transmitter 311 operatively configured with transmission control 194. Detection memory 291 is communicatively connected to the transmitter 311 and multifunctional sensor 215. Transmission control 194, receiver 312, encoder 313, and detector 290 are communicatively connected to detection memory 291. The detection memory 291 is communicatively connected to CMOS 142 and CPU 141. The CPU 141 and the CMOS 142 are communicatively connected to micro-electronic circuit 410 comprising at least an antenna system 109. Receiver 312, transmitter 311, and encoder 313 are communicatively connected to a battery cell operatively configured with the receptor 110.

Figure 8:
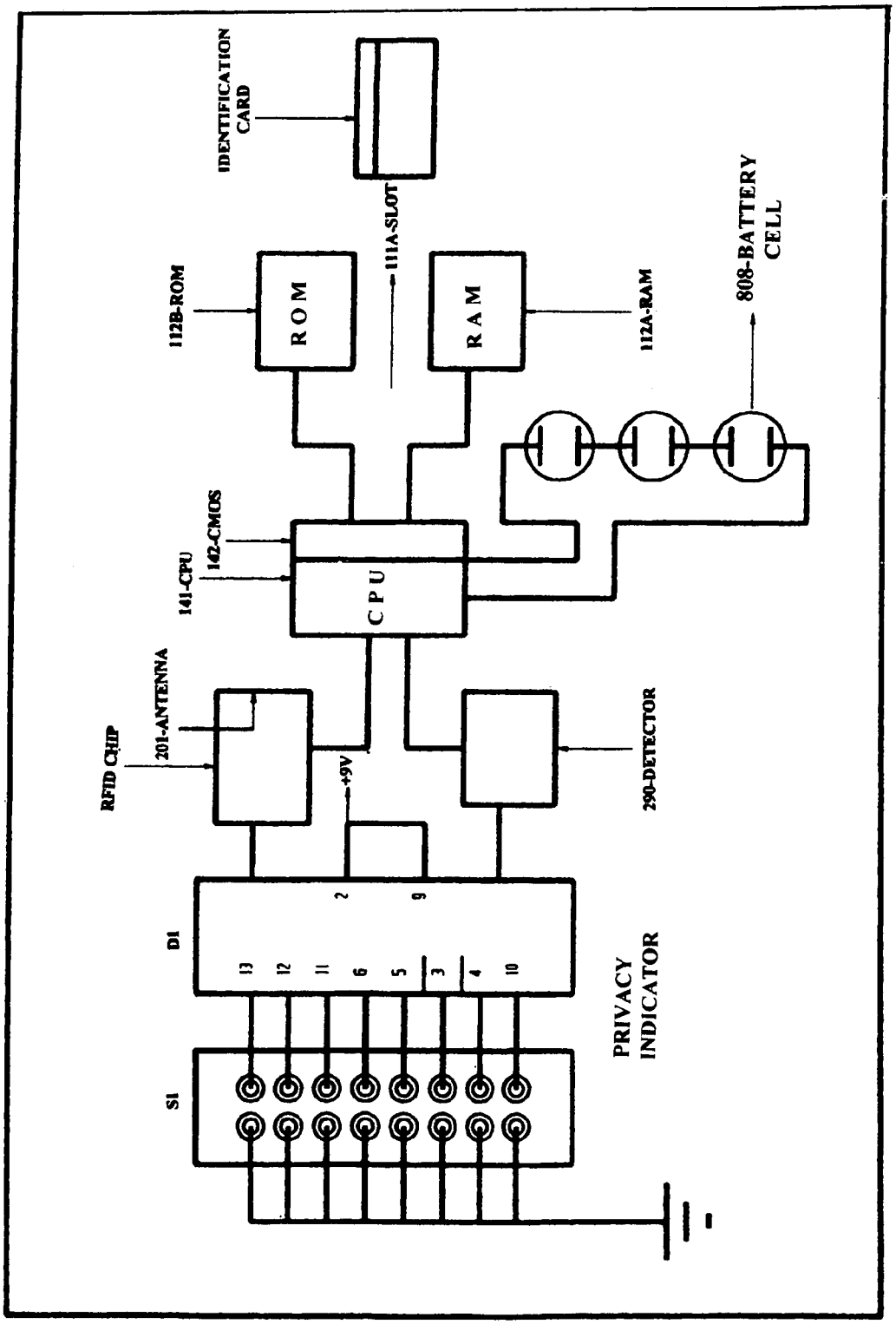
FIG. 8 is seen to represent a circuit diagram for the receptor privacy indicator with silicon battery cells.

Referring to FIG. 8 is seen an exemplary embodiment of the receptor 110 comprising a communication apparatus including privacy indicator. Switch (S1) is communicatively connected to RFID CHIP in communication with antenna 201. The common node display (D1) is operatively configured with at least an energy means operable for converting solar energy into electrical energy. RFID CHIP is operatively configured with antenna 201, further responsive to solar energy. A CPU 141 is operatively configured with detection device 290, and communicatively connected to at least a CMOS 142 being operatively connected to a battery cell 808. The receptor 110 further comprises an insertion slot 111A, operatively configured for checking identification cards at security stations and/or by homeland security agents. In one embodiment of the disclosure, trained personnel may request an identification card 112 from at least a suspect. The ID card 112 would then be inserted in the insertion slot 111A. The receptor 110 comprises IC card and/or SIM card comprising wireless communication applications in communication with software program operatively configured with the ROM 112B to read the ID card 112. The ROM 112B is communicatively configured to enable communications to the RAM 112A. The RAM 112A is responsive to the database 113 where such ID information may be stored for retrieval. A screen read-out 113A comprises a display device being configured with the receptor 110 responsive to full information about the suspect. Suspected person's information may be retrieved from at least database 113. An 8-pin privacy indicator switch (S1) is operatively configured with the receptor and responsible for communicating to an officer in private when a pre-used and/or post used weapon is sensed within the body of a suspicious person. Switch (S1) comprises of display selections corresponding to cathode A, cathode G, and cathode D of at least a 7-segment common anode display settings (D1). Chip 200a comprises a detection tool responsible for providing detections and communications to at least a security agency and/or the military and responsive to identifying threats or any object of terrorist attack or enemies at battle fields.

In other embodiment, the RFID chip 200a is coded and in communication with the IC card and/or the SIM card to identify members of the agencies such as battlefield personnel and other security personnel. Still in another embodiment, the RFID chip is configured to distinguish the said personnel from enemies at battle front and/or from terrorist personnel. The coding of RFID chip is responsive to detections, providing the receptor with data operable to provide means of communicating to trained security personnel and military personnel information about the detections with reliability, accuracy, and in real time alert. The information may include anticipatory act of terrorism and/or any mobility of enemy personnel in a battle field. Disclosed embodiment further provides an innovative approach to combating any future war. The technical characteristics of the RFID chip 200a and other sensors embodied in the nanotechnology applications provide many opportunities for innovation to combat the war of terrorism and any other war thereon.

Figure 9:
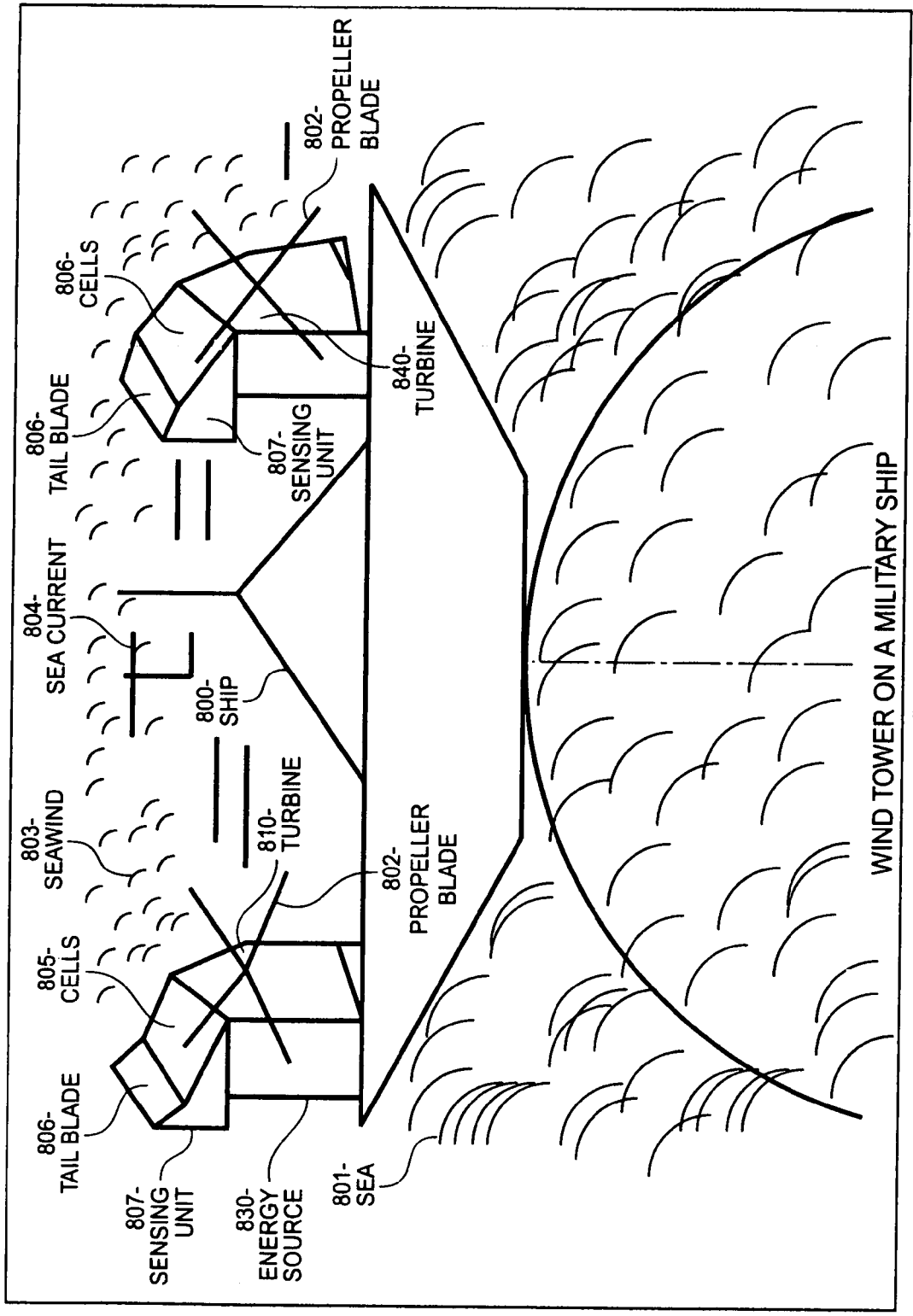
FIG. 9 is seen to represent a sailing military ship with wind towers for empowering military outfits and receptors.

Referring to FIG. 9 is an embodiment of a wind tower on a military ship. A battleship 800 is positioned at sea 801. The sea 801 consist of natural energy such as sea wind 803 and sea current 804. The battleship 800 is operatively configured with means to transform the sea wind 803 and sea current 804 into usable energy source 830. In one embodiment, the ship provide apparatus for transforming sea wind 803 and sea current into energy source 830. The ship 800 is configured with at least a turbine 810 and 840. In other embodiment, the turbine 810, 840 comprises at least a tail vane 806. In other embodiment, the tail vane 806 comprises at least a sensing unit 807. Yet in other embodiment, the turbine 810, 840 comprise of at least a propeller blade 802. Still in other embodiment, the tail vane 806 is configured with at least a cell 805. Yet, in still another embodiment, the turbine 810, 840 comprise of at least a wind tower 71 operatively configured with the tail vane 806 and the propeller blade 802. The propeller blade 802 is operatively configured to be powered by the sea wind 803. The tail vane 806 is operatively configured to enable the propeller blade 802 to rotate with the sea wind 803. The sea wind 803 comprises sea current 804. Disclosed embodiments provide the propeller blade 802 is rotatable so that kinetic energy is created along its movement. The kinetic energy along the direction of the wind is converted into mechanical energy by a generator apparatus being disposed with the turbine 810, 840 to generate electrical energy via the flow of sea current 804, which is then stored in cells 805. The stored energy at the cells 805 is transferrable to the receptors 110, which is normally carried by officers 35 as shown in FIG. 2.

Figure 10:
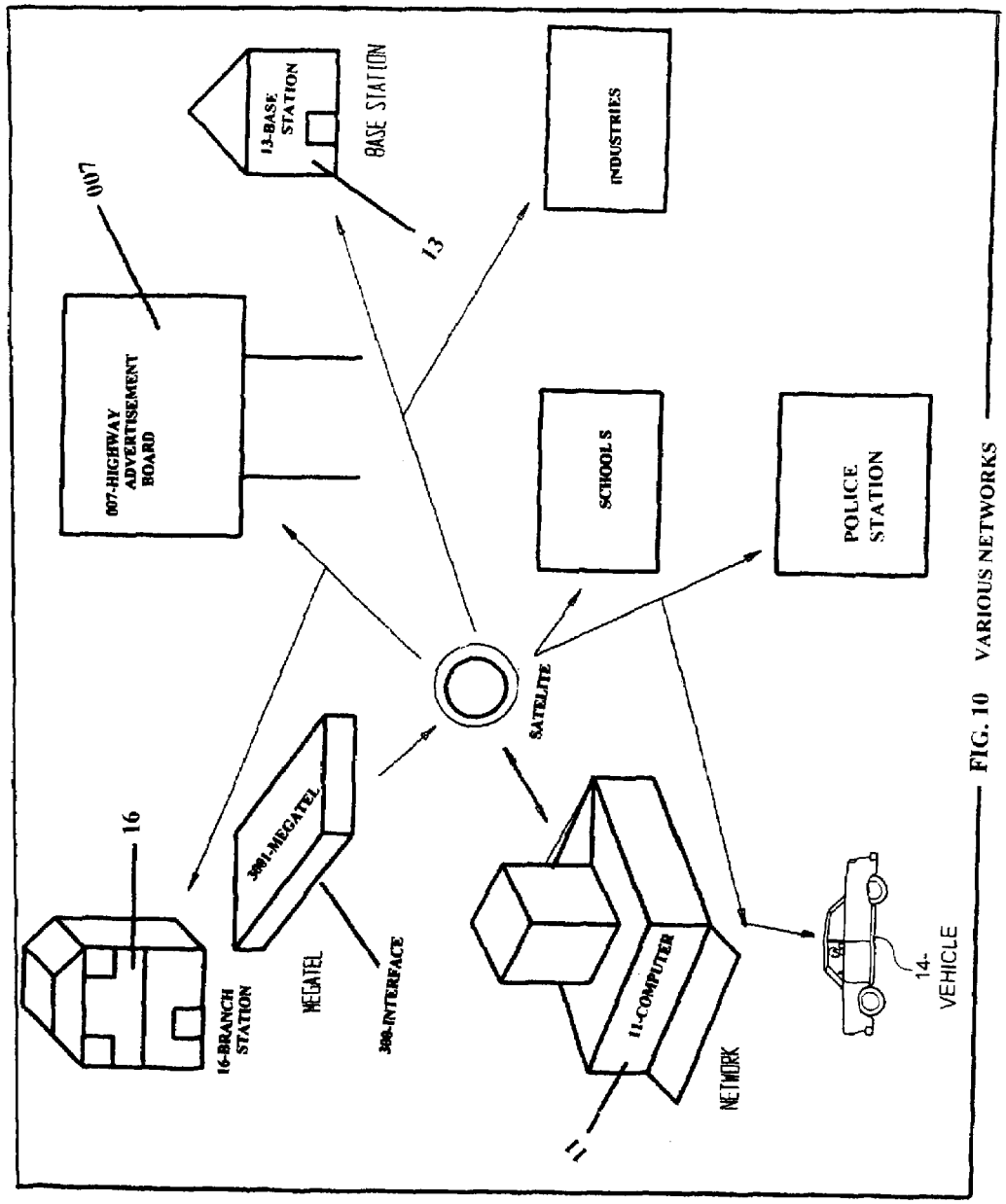
FIG. 10 is seen to represent various networks

Referring to FIG. 10, exemplary embodiments of various networks are shown communicable with the receptor 110, in communication with the outfit. Signals are transmitted through at least the interface 300, and 3001, and at least the satellite network, The interface 300 is configured for mega communications, and comprises mega telecommunication and information "megatel" interface 3001. Signals are processed and decoded within the receptor, and the decoded signals are transmitted through interface 300 and 3001. Interface 300 and 3001 are operatively configured with the receptor responsive to detection signal communications, and in communications with the central security monitoring station 70. Monitoring station 70 comprises at least a branch station 16, at least a base station 13, at least a police station, schools, and industries in communications with at least one another within a set network environment. The network further includes a computer 11, an advertisement board 007, a vehicle 14, satellite, and other stations.

Figure 11:
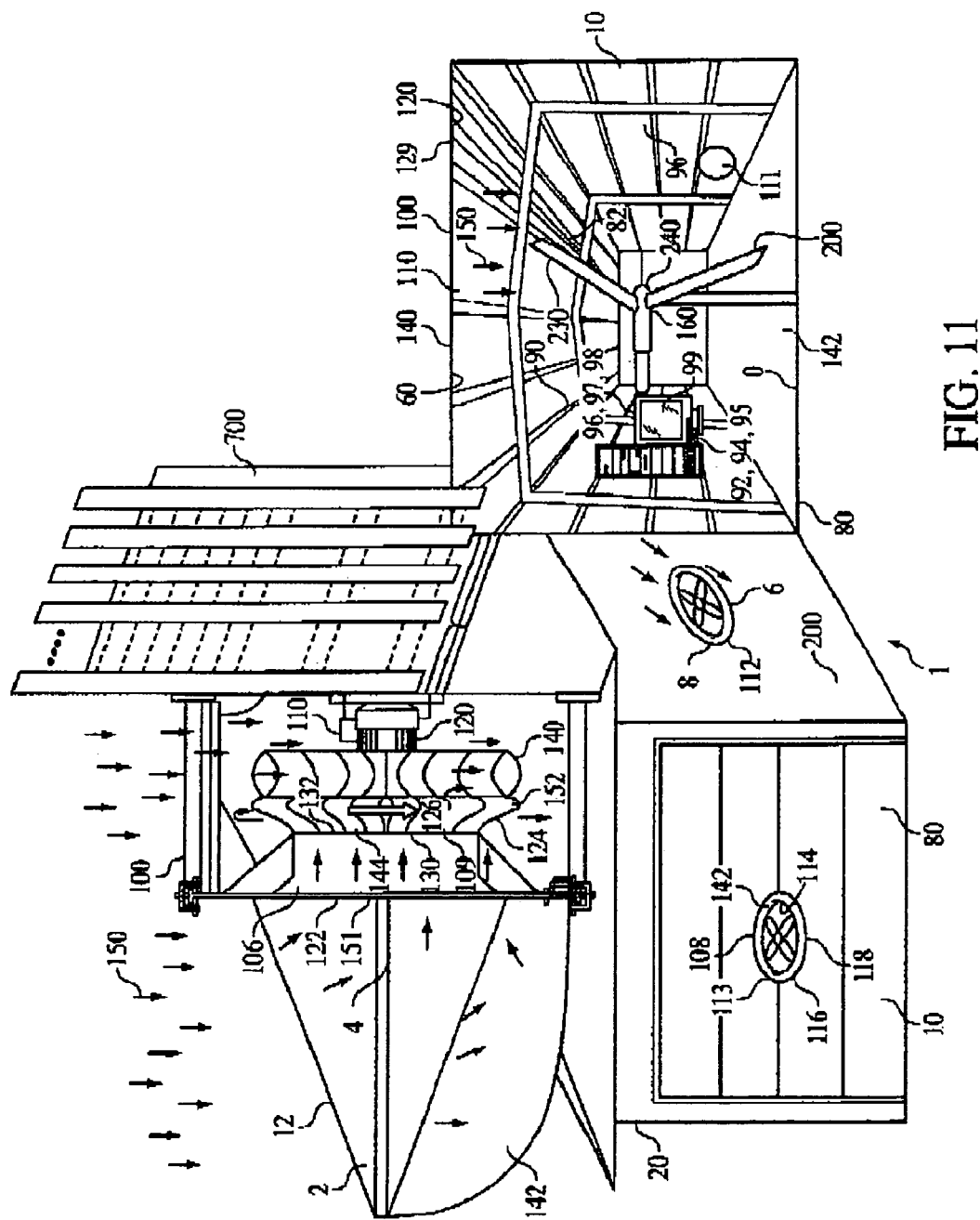
FIG. 11 is seen to represent a stationary wind tunnel, command post, and wind stations for enabling communications.

Referring to FIG. 11, further extension of the network environment comprises a wind fiber tower 71, a fiber tower network 69, a monitoring station 70, and a network 66.

Figure 12:
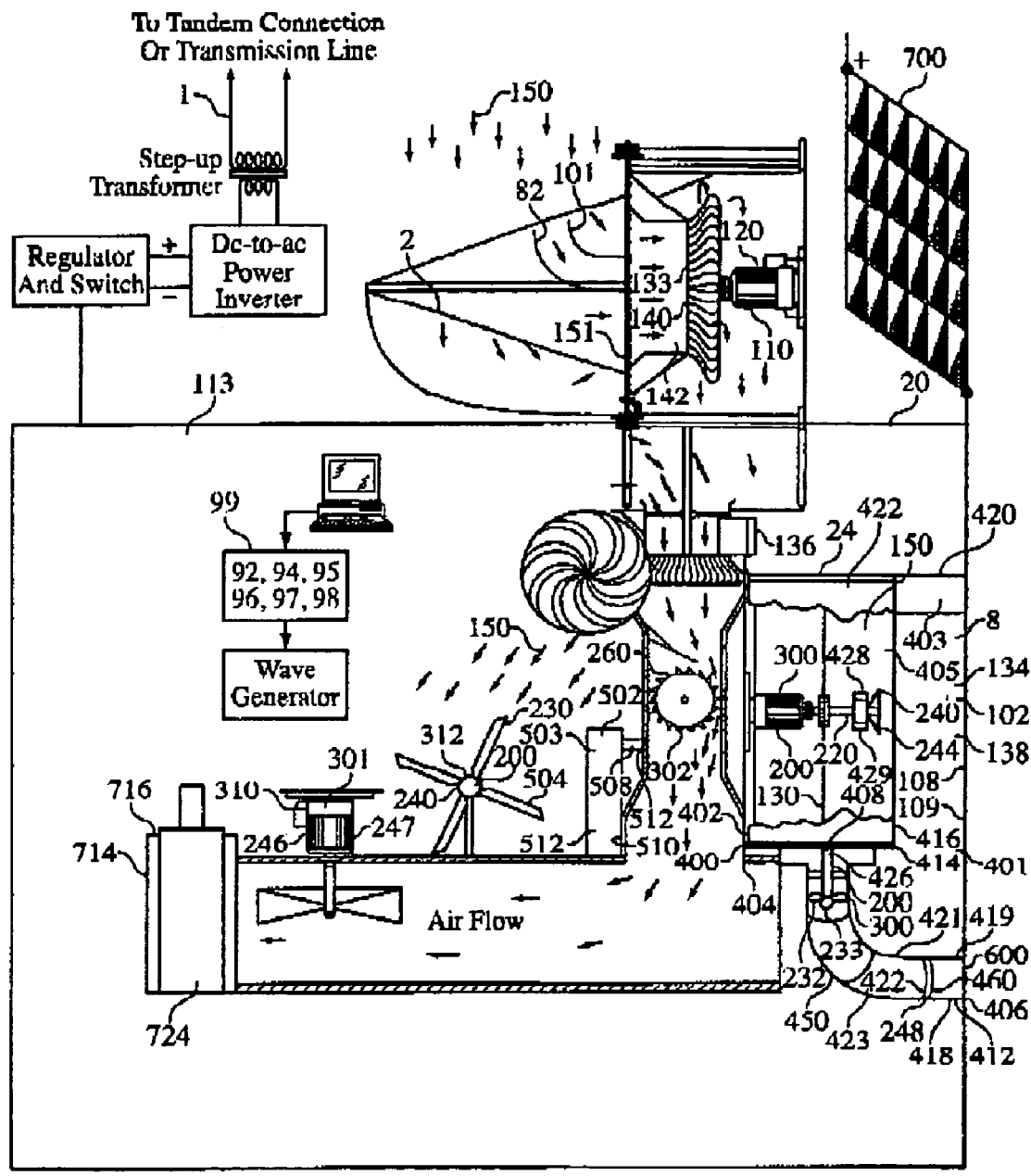
FIG. 12 is seen to represent a circuit diagram for receptor's random switching generator with receivers and transmitters.

Referring to FIG. 12, receptor 110 comprises a transmitter 242 and 311, and a receiver 243 and 312. Referring to FIG. 12A, the transmitter 242 comprises a battery which may be charged wirelessly. An amplifier is configured with the receptor for amplifying signal communications. The CMOS circuitry is operable to dissipate less power. Certain embodiments of the disclosure further provide a static logic configuration being operable on p-type and n-type metal-oxide-semiconductor field-effect-transistors "MOSFET's." being configured for implementing logic gates. Transmitter 311 and receiver 312 are communicatively connected to analyzer circuit 244. Referring to FIG. 12B, the amplifier is seen responsive to signal amplification. Transmitter 242 is seen operatively configured with receiver 243 and communicatively connected to connector beam 244. The amplifier is communicatively connected to receiver 243 and operatively configured with transmitter 242. The transmitter 242 and 311, and the receiver 243 and 312 comprise CMOS comprising of solar cells on n-type CZ silicon substrates, including Polycrystalline thin-film cells, lightly boron-doped CZ, or gallium-, indium-, and aluminium-doped CZ for converting solar energy, pressure force, sound wave, vibration, wind force into electrical energy. Disclosed embodiments further provide a thin-film comprising of thin layer of transparent conducting oxide, including tin oxide. Certain embodiments provide the oxides being highly transparent and configured to conduct electricity efficiently. Some embodiments provide antireflection coatings. Other embodiments provide Polycrystalline thin-film cells comprising tiny crystalline grains of semiconductor materials operable for converting solar energy into electrical energy. At least a CPU-1C1 is provided in communication with RFID chip reader-1C2. L1 and L2 are LED. S1 is an automatic momentary single pole double throw switch operative for transmitting and for receiving signals. C1 is an electrolytic capacitor being disposed on an energy platform comprising C2 and C3, which are imf capacitors. Q1 and Q2 are infrared LED emitter and M1 is a speaker microphone. R1 through R10 are resistors responsive to signals.

Referring to FIG. 13A, is seen further embodiment of a monitoring station 70 and a fiber tower network 69. FIG. 13B is seen an exemplary embodiments of officer 35, wearing outfit 10, 30, and 120. The officer 35 is seen outfitted with receptor 110, outfit 10, 30, 120, and 130. Adaptor 160 is seen configured with the outfits. The receptor 110 is communicatively configured and responsible for networking with the monitoring station 70 and the fiber tower network 69. The receptor 110 is further configured with battery cells, which are responsive to solar energy, pressure force, and further responsible for supplemental energy for empowering the detection platform. At least a fiber optic ribbon 240 is operatively configured with the outfit 10 and 10A, and responsive to supplemental connection between the receptor 110 through at least a connector 25. Referring to FIG. 13C is seen further exemplary embodiment of an Officer 35 being outfitted with disclosed embodiments. Disclosed embodiments further provide a detection platform, comprises nanotechnology applications within outfit 10 and 20. Referring to FIG. 13B and FIG. 13C are seen perspective embodiments of officers 35 monitoring a vehicle 50 entering an environment 60. A suspicious environment 90 is seen being detected with explosive 600 in a suspicious vehicle 50. Referring to FIG. 13D, the suspicious vehicle 50 is seen to have been stopped for inspection after the detection of at least a weapon.

Referring to FIG. 14, different configurations of nanotechnology applications are presented without any limitations to the scope of the disclosure. In FIG. 14A, outfit 10 is seen comprising a detection platform 295 configured with sensors 200 and 400. FIG. 14B is seen a supplemental configuration of outfit 10 comprising the detection platform 295 configured with sensors 200A and 400. FIG. 14C is seen another supplemental configuration of the outfit consisting of outfit 10A. FIG. 14D is seen further supplemental configuration of outfit 20 comprising the detection platform 295 being configured with sensors 200A and 200. In FIG. 14E, FIG. 14F, FIG. 14G, FIG. 14H, and FIG. 14I, are seen similar configurations of the detection platform 295 for outfit 10 and 20 consisting of nanotechnology applications.

Figure 15A:
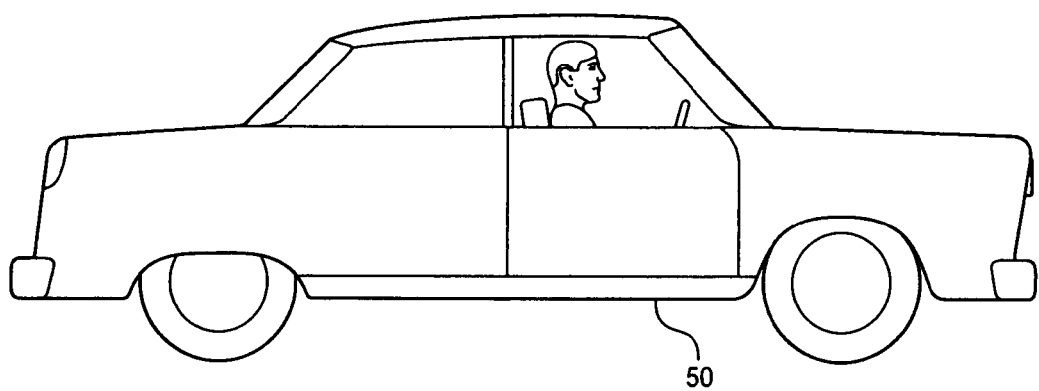
FIG. 15 is seen to represent military personnel whose uniforms have detected a vehicle that is equipped with explosives
Figures 15B, 15C:
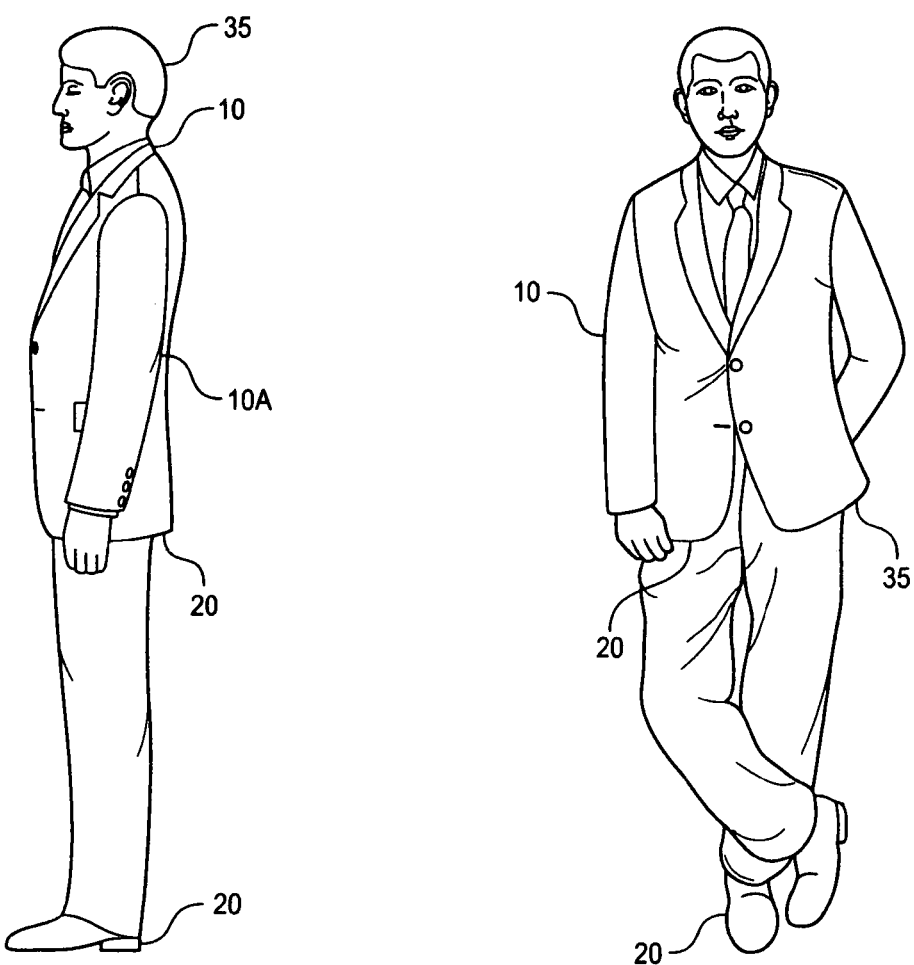

Referring to FIG. 15A, is seen perspective embodiment of a suspicious vehicle 50 carrying weapons of mass destruction being detected by disclosed embodiments. Referring to FIG. 15B is seen a first exemplary embodiment of the outfit 10, 10A, and 20 worn by an officer 35. The officer 35 is seen monitoring the detection of vehicle 50 as seen in FIG. 15A. Referring to FIG. 15C, is seen a second exemplary embodiment of the outfit 10 and 20 and worn by officer 35. Officer 35 is further seen monitoring the detection of vehicle 50 as seen in FIG. 15A.

Figure 16A:
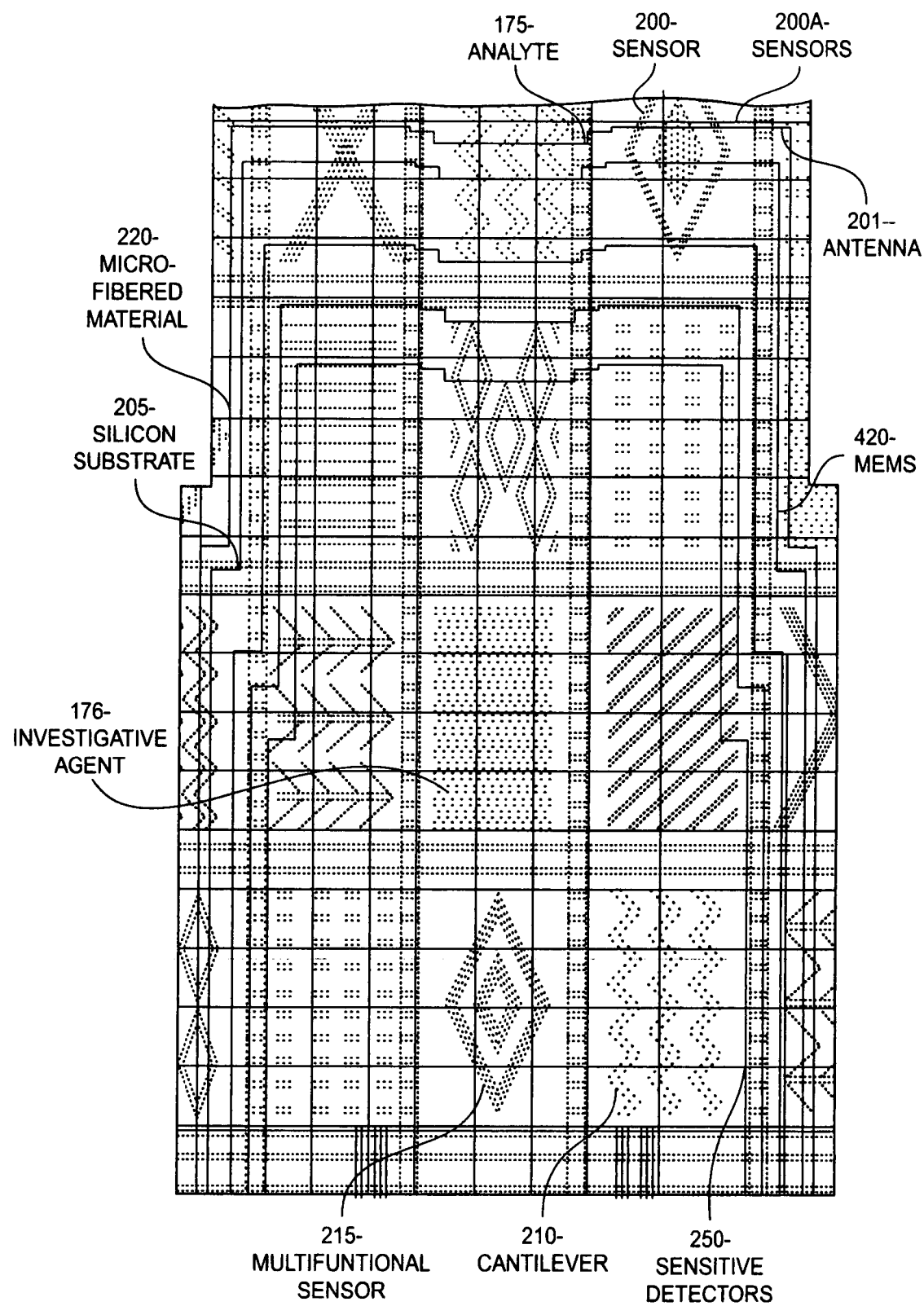
FIG. 16 is seen to represent a planned outline of the microfabric material with the embedded sensors.

Referring to FIG. 16A, is seen an exemplary embodiment of the material for an outline configured for providing a detection platform comprising a silicon substrate 205. Sensors 200, 200A, 210, 215, and 420 are embedded in the silicon substrate 205. The silicon substrate is fused and/or etched in micro-fibered material 220. The micro-fibered material 220 comprises of at least a material consisting of microfiber characteristics that exhibits excellent electrical properties. The detection platform further comprises an investigative agent 176 operatively configured with an analyte 175. Antenna 201 is embedded in the silicon substrate 205 and communicatively configured with sensors 200, 200A, 210, 215, 250, and 420.

Figure 16B:
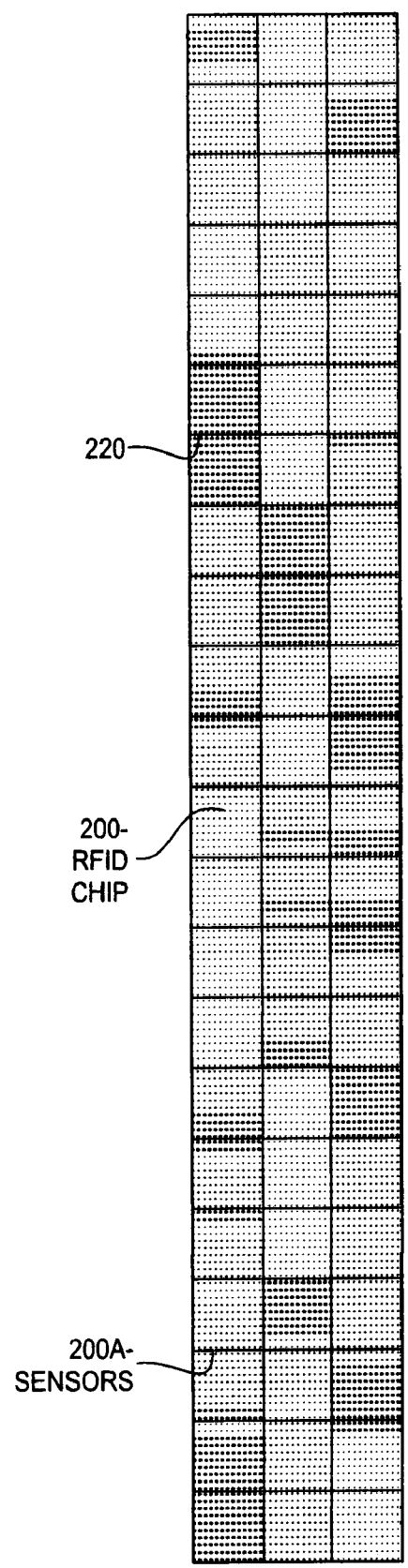

Referring to FIG. 16B, is seen further exemplary embodiment of the disclosure, providing perspective embodiment of the material for the detection platform, comprising microfibered material 220 configured with sensors 200 and 200A.

Figure 17:
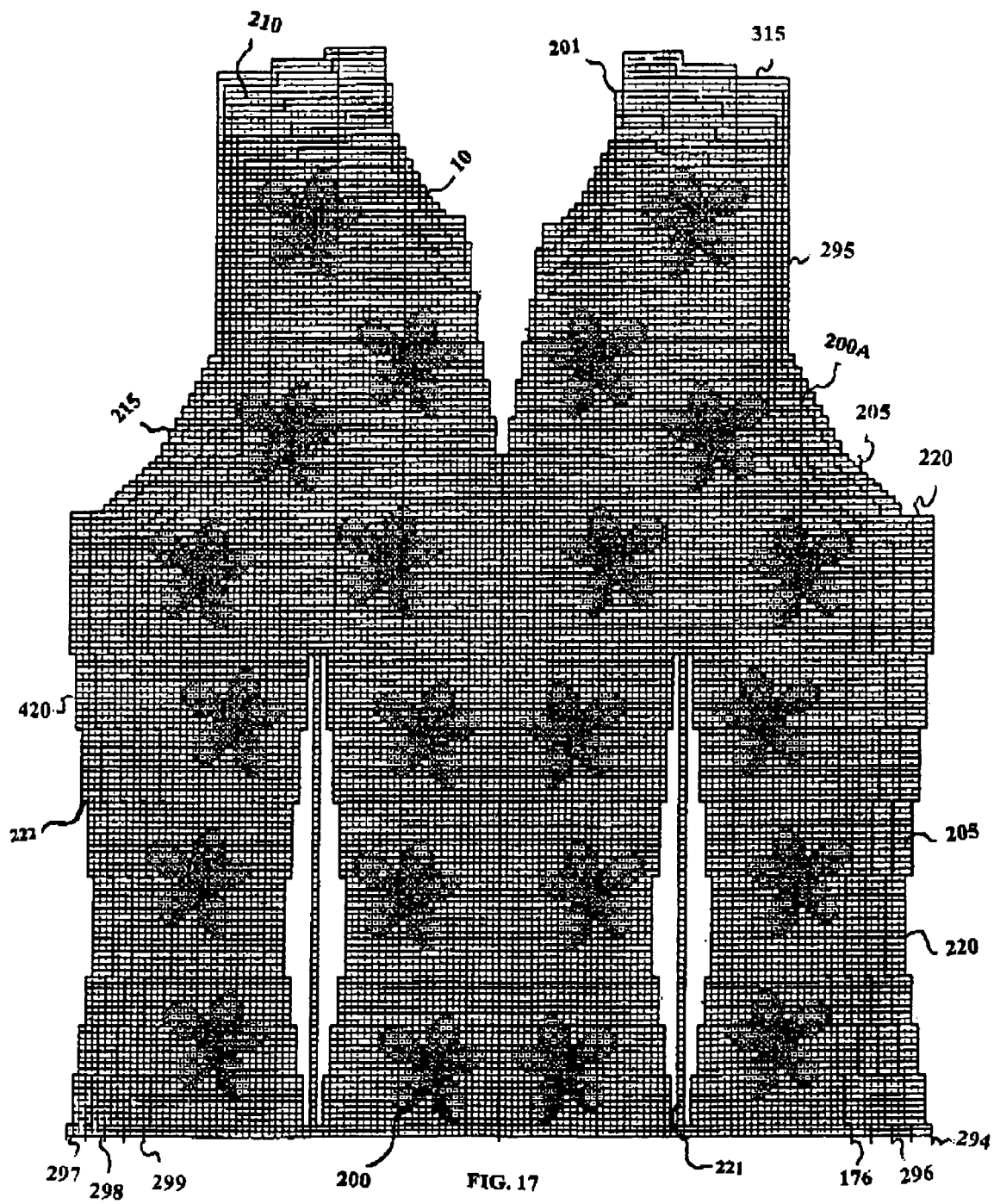
FIG. 17 is seen to represent a wired outfit for monitoring, protecting, and detecting.
Figure 12:
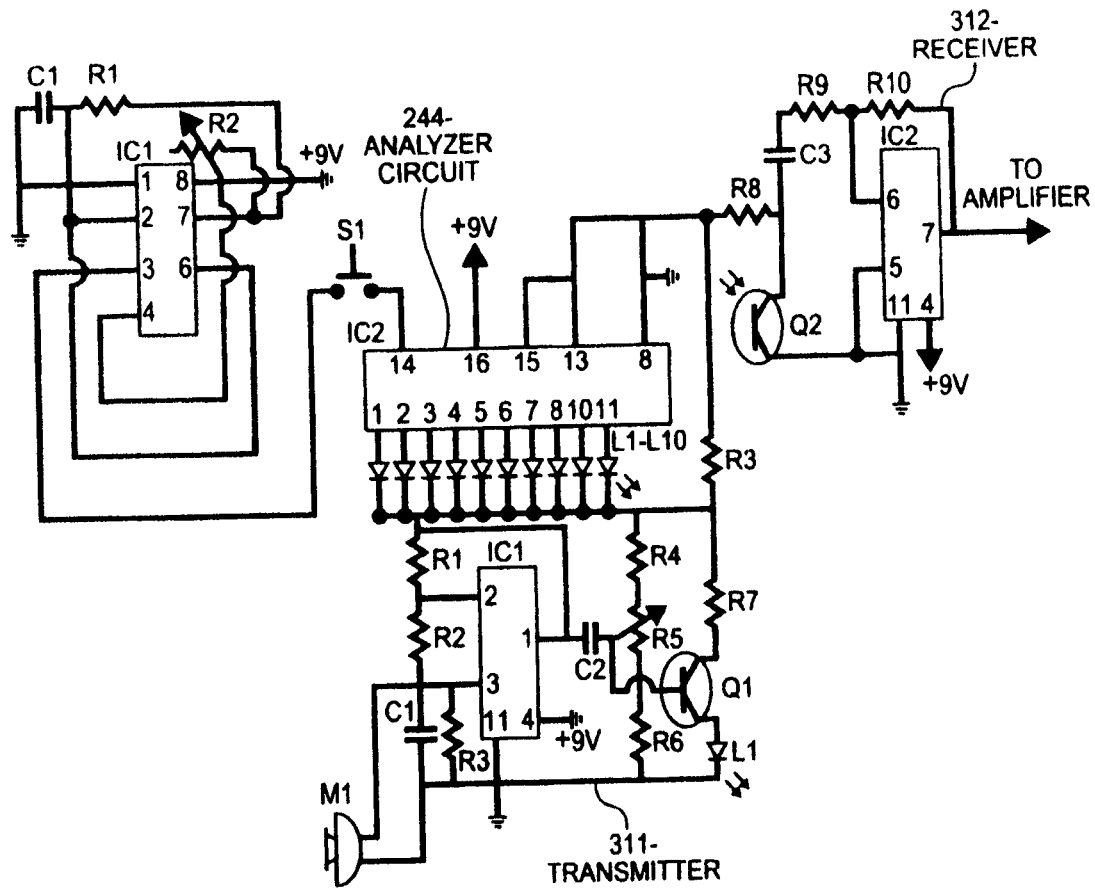

Referring to FIG. 17, is seen an exemplary embodiment of the outline for the outfit 10. Disclosed embodiments further provide sensors 200, 200A, 210, 215, and 420 being embedded in a silicon substrate 205 and etched/fused in a microfiber material 220 comprising at least a material with good electrical characteristics to provide efficient detection selectivity for the detection platform 295, energy platform 296, and cell platform 297. The detection platform 295 further comprises miniaturized steels comprising nano-wires being configured to provide electrodes 298. The outfit 10 is operatively configured to monitor, detect, and protect. The detection platform further comprises silicon substrate 205. Sensors 200, 200A, 210, and 215 are further embedded in the silicon substrate 205. In one embodiment, the silicon substrate 205 is further configured with ferrous and/or non-ferrous materials 221. In other embodiment, the material 221 is alloyed with the micro-fibered material 220. Still in other embodiment, the material 221 comprises malleability properties comprising a malleable miniaturized steel 222. Antenna 201 is embedded within the structures of the detection platform and communicatively connected to the sensors. Investigative agent 176 is operatively configured with analyte 175 and communicatively connected to the detection platform responsive to detection signal communications. Disclosed embodiments provide the detection platform 295 comprising electrical isolated layer 299 configured with infrared transmitter-receiver and/or transducer 315.

Disclosed embodiments provide an outfit method of detection comprising a detection platform consisting of sensors 200A, 200A, 210, and 215. Certain embodiments provide a sensory platform comprising MEMS 200, RFID 200a, TRANSDUCERS 315 and nano-sensors being embedded in a silicon substrate 205 and fused in a micro-fibered material 220 to enable the detection platform.

The detection platform of FIG. 17 comprises micro-fibered material 220 which may be etched on a second materials, including a non woven material being operable to produce a detection outfit 10 for homeland security and other security applications, including military applications and postal service applications. The outfit 10 is configured for detecting biological and chemical agents on work/public places and may be applicable in public water supplies. The silicon substrate 205, micro-fiber material 220, and the nano-sensors are unique to advanced detection sensitivity and selectivity. Disclosed embodiment further include ferrous and/or non-ferrous materials 221 alloyed with the micro-fibered material 220 and embedded, fused, or etched to provide material toughness and sensor durability of the finished product.

Still, other embodiment provides a wearable outfit detection method, further comprises malleable miniaturized steel 222 being alloyed with other materials to exhibit advanced toughness of the finished product for different applications. These applications further include police outfit, military outfit, or any uniformed law enforcement outfit. Certain embodiments of the disclosure provide a detection platform being configured to exhibit elastic properties. Some embodiments provide alloyed materials to enable the outfit 10 exhibits elastic shrinkage. In this approach, the outfit 10 may further consists of miniaturized micro-steel material 222 being operable for providing reinforcement within the structures of the silicon substrate 205 and/or the micro-fibered material 220. Disclosed embodiments further provide reinforcement to enable the detection platform exhibits toughness in various applications that include hostile environment where bullets may be exercised. The reinforcement of the detection platform further consist of other properties such as elasticity and/malleability within the structures of outfit 10. The reinforcement of the detection platform further comprising means for preventing bullets penetration through the outfit 10. In other embodiment, the methods further consist of alloying the miniaturized steel material 222 with micro-fiber material 220 such as polypropylene in a silicon substrate 205. The silicon substrate 205 is operatively connected to/etched on the normally used material for military and/or uniformed law enforcement outfit.

The advancement of nanotechnology application to wearable outfit 10 further requires the biological sensing elements to be selectively recognized as a particular biological molecule through a reaction specific adsorption, or other physical or chemical processes. Transducer 315 is further configured for converting data results into usable signals, which are quantified and amplified, and communicable to a network. The transducer 315 may consist of optical, electro-optical, or electrochemical devices, providing many sensing opportunities such as tailoring biosensors for specific detections. The transducer 315 further comprises means for translating physical or chemical changes within the detection environment into useful signal communications by recognizing an analyte and relaying its analysis through electrical signal communication. The electrical signal communication is initiated from the detection platform in communication with the receptor 110. Further development of the outfit 10 via nanotechnology applications would provide homeland security intelligence with the proper tool for monitoring and better response to detection, protection, and communication.

Referring to FIG. 8, is seen further embodiment of the receptor environment being configured for empowering the detection environment and for propagating through in-depth detection analysis, eliminating false communication while providing at least a communication with a network. The detection platform in response to the environmental problem is essential for the application of disclosed embodiments.

In FIG. 4 is further seen the nanotechnology approach to providing the detection platform 295. The detection platform 295 further includes RFID chip 200a. The RFID chip 200a is embedded in the silicon substrate 205 and fused/etched in micro-fibered material configuration. Disclosed embodiments further provide nano-sensors in a silicon substrate 205 and fusing the silicon substrate in a micro-fibered material 220 for providing reinforcement in pipeline applications for the detection of elements flowing within the pipe line. In this regard, the RFID chip 200a is configured in a similar fashion, providing a sealant made out of the silicon substrate configuration with the micro-fibered material 220.

The sealant could be in the form of an O-ring being used for the construction of a valve, such as a butterfly valve for water pipeline monitoring. Disclosed embodiments provide methods of detecting objects flowing within the water lines, and consisting of RFID chip 200a serving as a numerical identifier being responsive to automated flow data within a closed system comprising a flow pipe.

Embodiments further provide the detection platform being disposed on the flow walls of the flow pipe, while the RFID chip 200a positioned at the flow valve, which analyzes all data signals and enables communication if detection or threat is eminent. Certain embodiments provide analytical methods of contextual detection within a closed system.

Disclosed embodiments provide advanced detection method for Homeland Intelligence Systems Technology "H-LIST," comprising an outfit 10a normally worn by officers, security officers, TSA officers, FBI, CIA, custom officers, boarder patrol officers, military officers and the like. The outfit 10A is operable for detection of deadly gases 700, and explosives 600, such as any weapons of mass destructions. Referring to FIG. 15, a receptor 110 is configured for analyzing information and for transporting the analyzed information wirelessly to a central security monitoring station 70 or networks. The timely response of receptor 110 speedily prevent any use of such weapons, and would advice occupants to depart from such environment 60 as seen in FIG. 2, where one of such weapons such as gases 700 had been used.

FIG. 1 is further seen comprising a piezoelectric device being operable with a piezoelectric crystal 260, which allows antibodies 270 to be coated to provide multiple use potentials in a solid, liquid, gaseous and explosive detections in all environment, including military, customs, CIA, FBI, chemical firms, biological firms, radioactive firms, healthcare, hospital facilities, commercial industries monitoring and healthcare monitoring, transit buses, buses and transit trains, airports, nuclear power plants and the like. The piezoelectric device further comprises immunologically active sensing element in the outfit 10a, being configured with electronic transducer 315, further responsible for sensing antigen/antibody concentrations by direct changes in the transducer output. The transducer 15 is further responsible for converting immunoreactions activities into different physical signals.

Certain embodiments provide antigen/antibody affinity reactions which are identified directly by measuring the frequency change of an environment, which corresponds to a mass change of the sensor surface. Some embodiments provide a detection platform method on an outfit operable for high sensitivity and lower power supply automation to enable specific detection of deadly weapons. Perspective embodiments consists of antibody coated piezoelectric quartz crystal transducer 315, comprising in signal-processing systems, operable for causing coated crystals (A) to selectively vibrate at fundamental harmonic frequencies. The coating traps particulates that change the effective mass 265 on the sensing surface and configured to enable a change in oscillating frequency of the antibody-coated crystal (A). The change in the oscillation provide signal communication through receptor 110 to the central security monitoring stations 70 and other agencies 80 or networks. The receptor 110 is responsive to detections, identifying the chemical and biological mass that has been detected based on the impacted crystal or specifically on the coated region of the recognition pattern. The device particularly employs transducer 315 for detection and integrates with the piezoelectric crystal technology.

Antibodies 270 as seen in FIG. 1 are coated on the crystals of the piezoelectric 260 and/or the surface of the microprocessor electronic 180 of FIG. 6 at specific harmonic nodal positions to enable detection of a change in mass that will cause a change in the frequency of the associated harmonic. Disclosed embodiments further provide detection configuration to detect a change in mass 265 that changes harmonic frequencies of the detection material. FIG. 6 further shows a functional block diagram of the receptor 110, being operatively configured with sensors 200 to provide further detection of the presence of particular biological and chemical explosives. The receptor 110 further enables detection of oscillating frequencies of two crystals due to their absolute frequency shift. A transmitter 311 is configured to generate radio frequency signals and sends detected signals to a frequency-modulating receiver 312. The FM receiver 312 receives signals from the radio frequency identification "RFID" chip 200a through the chip's antenna 201 Signals are decoded and send to the central security monitoring station 70. These signals could be sensed agent based on the pattern recognition of the foreign wave in the radio wave frequencies and the like. The sensors 200 or 200a, and decoder 314 are operatively connected to a detection memory 291 responsible for repetitive signaling. The encoder 313 and the transmission control 194 are operatively connected to an analyte chamber 195. The frequency transmitter 311 is connected to the encoder and the transmission control 194, providing real time interactive control means, detection means, and communication means to fiber towers or networks 69.

The transmission control 194 provides information about status of the detected agent to avoid false recognition due to unidirectional pressure effect on the wave's path. Signals are coded and sent to and from the transmitter 311 to the FM receiver 312. The transmitter 311 transmits continuous and repetitive coded signals until they are received by the central security monitoring station 70 or network 69. The sensors 200 or 200a, transmitter 311, detector 290, and the FM receiver 312 are the basis of the wireless communication responsive to homeland security monitoring. The outfit 10 provide uniformed army personnel or officers 35 the ability to monitor the deployment of deadly agents and the detection of other weapons of mass destruction within a defined environment.

FIG. 2 further shows Officers 35 wearing outfit 10a, which is etched with plurality nano-sensors 200 or 200a. Officer 35 is further seen assigned to a detection zone, battlefield, or environment 60 for monitoring plurality characteristics. The outfit 10 is configured for monitoring and detecting weapons of mass destructions and also the physiological conditions of personnel within the vicinity of the detection. The receptor 110 is configured such that the detection of anticipatory suspicious person carrying deadly gas 700 or explosives 600 will not only produce limited visual or audio signal, but would rather inform the officer 35 through other means, such as vibration, while wirelessly communicating to a central security monitoring station 70, wind fiber towers 71, or at least a network 69.

Disclosed embodiments provide radio frequency means on its RFID chip 200a or receptor 110 to receive and transmit sensed data. Receptor 110 may comprise a cell phones 111 and two-way radios 112 being operable as auxiliary receptors to further add protection in the homeland security monitoring. In other embodiment, sensor 200 is seen to represent at least an RFID chip 200a in the size of at least a human hair.

Referring to FIG. 13B and FIG. 13C, outfit 10, 10A, 20, 20, 120, and 130 further comprises chip 200a embedded in the silicon substrate 205 and etched in a micro-fibered material 220. Disclosed embodiments provide a detection platform on an outfit comprising sound wave apparatus for tracking communication between terrorist networks and the like. Outfit 10, 10A, 20, 20, 120, and 130 are responsible for providing interactive communication thereof and for detection of weapons of mass destruction. The configuration of the outfit 10, 10A, 20, 30, 120, and 130 is such that antenna 201 is etched in the chip 200a and faced outward to track foreign objects traveling through the wind waves. The chip 200a is embedded in a silicon substrate, the antenna 201 is operatively configured with the chip 200a. The chip 200a and the antenna 201 are embedded in the silicon substrate 205 and etched in a micro-fibered material 220 providing a fabric material for the outfit 10, 10a, 20, 30, 120 and 130. The outfit is communicatively configured for wireless communication network and mobile detection apparatus for detection of weapons of mass destruction. In another embodiment, the detection platform further comprises sensors in silicon substrate and micro-fibered material 220, providing sound wave detection apparatus operable for innovative military outfit being configured with chip 200a coded to detect enemy personnel and persons, such as a terrorist carrying at least a weapon 600, or guerilla fighters in their normal hidings, such that detections are enabled and communicated to networks 69 or command post 70 or 71 as seen in FIG. 11.

The outfit 10, 10a, 20, 30, 120, 130 is designed to receive input signals and to send out output signals through the embedded antenna 201, configured for gathering data (such as physiological condition of a fallen soldier) and for providing communication indicative of the physiological conditions of personnel, whether or not they are alive. Disclosed embodiment provide a system that monitors heart rates, vital signs, blood pressure and respiratory system; and provide communication to at least a network if the heart stops beating or the respiratory system under goes a drastic change. Certain embodiments provide apparatus for modernizing homeland security and battlefield personnel with wearable digital combat gears to protect against any act of terrorism and/or guerilla style attack, wherein all field communications are connected to at least a common network 69, 70 and 71 seen in FIG. 11. A typical example of a common network 69 is at least, the equipment used in a battlefield to attack enemies or to monitor enemy movements, wherein detection and communication to battlefield personnel is enabled through disclosed embodiments. By networking homeland personnel and/or army personnel, whether independently or collectively, allows a cohesive integration and collaboration through wirelessly sharing of field data to enable real time responses and provide devastating force of action towards weakening enemy lines. In a similar example of a typical network, the embedded antenna 201 in the RFID chip 200*a* or sensor 200 comprises retractable devices that read information traveling through waves. This information may travel through radio waves or microwaves. Disclosed embodiments provide apparatus for communicating such information wirelessly to command post computers or at least a common network station computer for further analysis and instructions to expedite responsiveness.

Referring to FIG. 13B, the disclosure provide outfit 10, 10*a*, 20, 30, 120, and 130 in communication with receptor 110. The chip 200*a* is configured to emit beams through the antenna means 201, invisible beams that will travel through waves, such as radio waves, micro-waves, ultrasonic waves and the like. Each emitting wave is responsive to current travelling through trained pattern and reading information that would provide the exact location of weapons of mass destruction, or the activities in anticipation of weapons of mass destruction, or the location of enemy personnel. Disclosed embodiments further provide radio frequency identification chip 200*a* "RFID CHIP" being configured with embedded antenna 201, wherein both the chip 200*a* and the embedded antenna 201 are further embedded in a silicon substrate 205 operatively configured with GPS technology and then etched in a micro-fibered material 220.

The micro-fibered material 220 as seen in FIG. 17, is alloyed with non-ferrous material such as at least silver micro-fibers, innovatively re-enforces the fabric and enabling a wired outfit 10*a*, further comprising pathogen detection apparatus. It is anticipated that the disclosure of a non ferrous micro-fibered material 220 within the structures of the fabric for the outfit, such as silver micro-fiber in particular, would improve the electrical properties of the material, respond to temperature conditions, convert solar energy into electrical energy, and provide a platform for pathogen detection. Disclosed embodiments provide apparatus to enable rapid responses to bacterial in human bodies. These bacterial is normally created by the environmental condition of the site, such as biological agents 630 or chemical agents 620 in the air. Such that, in a real severe environmental weather condition, the electrical properties of the silver micro-fiber 220 will reverse or bias the situation, enabling the system to thermostatically operate partly as an HVAC control system's outfit 10*a*, partly as an outfit 10*a* comprising anti-bacterial device that fights biological and chemical agents that could possibly come in contact with the skin of a personnel wearing the said outfit 10, and largely as a protective and monitoring outfit 10*a* device for the detection of weapons of mass destruction. The silver micro-fiber 220 is further responsible for tracking physiological conditions of army personnel, wherein communication is enabled when any of such detection is sensed. Once the chip 200*a* encounters any detection of wavelike particles, wireless communication means is enabled through the receptor 110. The receptor 110 further comprises means for amplifying communication signals to a network 69 of security agents or military personnel. Such network 69 includes wind towers 71 for tracking down other terrorist activities and interactively communicating with personnel wearing the outfit.

Referring to FIG. 8, the receptor 110 is further configured with an insertion slot 111*a* configured for checking identification cards to be used by homeland security agents. In this embodiment, trained personnel would request an identification card 112 such as a driver's license from a real suspect in anticipation of an attack and insert the ID card 112 in the slot 111*a*. Inserting the driver's license into the slot 111*a* of the receptor 110 will enable the ROM 112*b* to read the ID card 112 and communicate to the RAM 112*a* to access the database 113 where such ID information is stored for retrieval. The receptor 110 is further configured with a screen read-out 113*a* responsive to information about the anticipatory suspect being retrieved from at least database 113 containing drivers licenses or a common network of HIT-LIST. Disclosed embodiment provide an 8-pin privacy indicator (S1) operable with the receptor to communicate to an officer in private when a weapon is sensed. The indicator include a switch S1 in communication with the display selector and corresponds to cathode a, cathode g, and cathode d of a 7-segment common anode display settings (D1). The chip 200*a* is configured with the receptor and acts as a detection tool. The receptor 110 comprises a communication means for applications in global homeland security agencies and/or the military, making it very possible for agencies to identify threats or any object of terrorist attack or enemies at battlefields.

The RFID chip 200*a* is further coded, comprising GPS technology being operable to identify members of the agencies such as battlefield personnel and other security personnel, and is configured to distinguish personnel from enemies at battle front or terrorist personnel. By coded the chip 200*a*, the system provides means to feed trained security personnel and military personnel with reliable, accurate, and real time information about anticipatory act of terrorism or any mobility of enemy personnel in a battlefield. Certain Embodiment provides innovative approach to combating any war, including the war against terrorism and any other war thereon.

Disclosed embodiments further provide an outfit method of equipping airport personnel to be efficiently pro-active in their assignments. Some embodiments provide apparatus operable to read off information in a wallet, pocket book, or luggage and single out any one of such luggage if detected or suspected of any weapon for extra checks, providing a vision possible in H-LIST. Certain embodiments provide a computer implemented method, comprising a communication apparatus in communication with a detection platform consisting of the fabric material being used for the outfits and providing wireless communications and mobile detection of weapons of mass destruction, including conduction of body heat and anti-bacterial means.

In another embodiment, the combination of the silicon substrate, the metal oxide and/or thin film or miniaturized metallic material with the chip 200*a* provide an energy platform on the outfit comprising battery cells configured for converting solar energy into electrical energy, and may include a battery-powered fabric for the outfit 10. The energy platform is operable with receptor 110 to amplify detection pattern of weapons of mass destruction. Certain embodiments provide energy platform comprising of a silver microfiber 220 responsive to anti-microbial composites, for covering wounds, for dressing, and for cloths. The energy platform in communication with the detection platform to provide the ability for the outfit to eliminate static electricity by dissipating the static electric charges. Disclosed embodiment further provide a detection platform configured with a processor means, comprises a pattern recognition technique for producing "Sensing," a controlled communication signal and communicating any sensed detection to a wireless modem or control module being operable to provide wireless communications to security monitoring agencies or network 69. The network is responsible to optimize the protection against terrorism and monitoring the mobile capabilities to assigned terrorist locations. Disclosed embodiments provide the energy platform comprising a cell platform being further configured for medical devices applications. Other embodiments of the cell platform comprise communication applications. Disclosed embodiments further provide the cell platform comprising nickel-cadmium (NiCd) configured with nickel oxide hydroxide and metallic cadmium. Disclosed embodiments provide the nickel oxide and metallic cadmium further consisting electrodes being configured for deep discharge applications. Other embodiments provide methods and systems for storing electrical energy, comprising the cell platform. The cell platform includes battery cells and/or capacitor configurations for withstanding higher number of charge/discharge cycles and faster charge and discharge rates. Certain embodiments of the cell platform further comprise an electrode device comprising at least electrically conductive nano wires/tubes being coated with at least one electrically isolating layer.

The system as seen in FIG. 4, also accepts input from security agents, security agencies, security stations, and guards in anticipation of a terrorist act, such as suicide bombing. When such detection is eminent, disclosed embodiment would provide communications through wind pattern towers to reach other agencies for immediate reaction. The pattern recognition technique as disclosed processes signals that are generated by objects and the said signals are periodically modified by interacting with other objects in order to determine which of the classes the objects belong to, including radioactive, biological, chemical, and explosives. Certain embodiments provide apparatus that generates signals based on the detection of at least a class of the object. Disclosed embodiments further provide apparatus that determines if the object is of a specified class and then assigns the object to the specified class code, or sends out other signal if the object is not a member of any of the coded classes in the set. The signals thus generated are electrical signals and emanates from at least a transducer 315. The transducer 315 is seen to be very sensitive to radiation originating from weapons of mass destruction. Some embodiments provide apparatus for anticipatory sensing pattern recognition technique and providing communication to network 69 in anticipation of terrorist activities.

In other embodiment, sensors 200 and 200a are etched in a silver fibered material 220 to form a bimetallic layer, providing antibodies of chemicals and bio-molecules responsible for detection of high explosive substances in their solid, gaseous, and liquid phases as seen in FIG. 3. The bimetallic layer is mixed with other substances at different points of their embodiment, providing a highly specified detection platform for terrorism device applications. Certain embodiments provide mixtures of micro-layers consisting of surface plasmon resonance spectroscope on the surface of sensors 200 and 200a. Other embodiments provide etching/fusing the combination on a silver micro-fibered material 220 to provide a highly sensitive detection device for anti-terrorism application. These teaching combinations are highly reliable for security monitoring and for detection of weapons of mass destruction. The teaching further requires portable, mobile and wireless detection devices to be configured with networks 69, wind station networks, satellite networks and the like as seen in FIG. 10. Disclosed embodiments provide an innovative approach to security and monitoring, including all branches of exposures, such as military, Government, law enforcement, hospitals, industries, recreational facilities, athletes, sporting events and facilities, amusement facilities and the like.

The receptor 110 further empowers the outfit 10a to enable high specificity and low detection levels for various design application of security and monitoring, and the detection of weapons of mass destruction. Embodiments provide the receptor 110 being configured for amplification of the embedded sensors to allow speedy detection within a mobile environment. Embodiments further provide an innovative method of detection. Its wireless communication means to network stations provides convenience to use. The receptor 110 is very specific in its analysis and it is self-diagnostic. The receptor 110 provide detection of contraband substances within a container or luggage. CPU 141 enables interface between the sensors on the outfit 10a, the receptor 110. The network stations responsive to enable interactive communication thereof when detection is eminent. Detection of vapors emanating from explosive substances and weapons of mass destruction is timely, such that when a particulate matter is emitted from its substance, its concentration or presence will immediately be detected. Communication is then enabled from the detection environment to the network stations 69, which are classified and/or unclassified for security monitoring of at least a nation.

The receptor 110 functions both as an amplification device and also as a control/communication system. The receptor is responsible for controlling and processing the overall detection analyses instantly, and for providing wireless communication to at least a network station. The detection apparatus provide constant monitoring and requires no tunnel for people to walk through. The system detects these people as they walk pass a person wearing the outfit 10a. Its mobile detection means is portal and invasive, preventing any act of suicide bombing or other acts of terrorism while also providing a non invasive detection means when the particulates in the wind waves are non destructive. Embodiments provide detection of explosives or contraband emission from concealed substances on individuals, luggage, vehicles, trashcans, airplanes, buildings, and other areas where such weapons could be used. Because many particulates of substances can be contained in wind waves, the sensors on the outfit 10a are outlined and configured to single out each concentration of various particulates that may be sensed or detected within terrorist networks. The outfit is further configured with plurality sensors being configured for providing effective sensitivity and reliability to detections. Embodiments further provide absolute solution for advancing critical analysis of weapons of mass destruction.

The silver micro-fibered material 220 as seen in FIG. 16 and FIG. 17 also serves as a filter element, providing a sensing medium to absorb particulates for analysis in their mobile environment. The antenna 201 also provides a thermal means to vaporize and evaporate the particulates to increase selectivity and sensitivity for detection. The outfit is further configured to thermostatically provide HVAC means in response to other environmental conditions to burst reliability under all weather conditions. The communication devices for the central security monitoring station 70 are configured with the receptor 110, which enables communication with various stations through transmitter 311 as seen in FIG. 6.

A microprocessor 140 is connected to memory 291 of FIG. 6 through input and output interface 300 to the analyte chamber 195. The receptor 110 further includes an antenna system 109 being operable for receiving radio frequency signals from the sensors 200 and/or 200a of FIG. 16 and FIG. 17, which are empowered by the transmitter 311. The receiver 312 and decoder 314 of FIG. 6 process signals, and decoded signals are then transmitted through the interface 300 and 3001 to the central security monitoring station 70 or network 69 and other agencies 80 of FIG. 11. The receptor interface 300 and the central security monitoring station interface, wind towers 71, or other networks such as megatel 3001, vehicles 14, computers 11, base stations 13, branch stations 16, highway advertisement board 007, industries, police stations, and schools as seen in FIG. 10, are communicatively connected through wireless links or modem to radio frequency or infrared links.

The receptor powers the outfit 10 through a fiber optic ribbon 240 or wireless connection means 241 as seen in FIG. 12. The wireless connector beam 241 includes a transmitter 242 and a receiver 243 being operable with at least a 9 Volt power for its initial energy, and may be charged wirelessly through the silicon battery cell 808 configuration as seen in FIG. 8. The silicon battery cell 808 is represented in FIG. 12 as +9 V, and is the central energy source and empowers the amplifier to enable active emission of beams of electricity over the sensing surfaces of the outfit 10. The outfit is comprises of silicon substrate microfiber configured to convert solar energy, vibration, sound wave, and pressure for into electrical energy. Because the sensitivity of the wireless connection depends on the light in the environment, the transmission and reception quality is then enhanced by shielding the IR LED and the phototransistor by focusing the IR beam with lenses. The potentiometer is adjustable to get the best possible connection signal. The wireless connection is a secondary connection means when the fiber optic ribbon or cable connection becomes faulty. The wireless connection further comprises infrared transmitter and receiver operable to transmit energy to the sensing medium. Since the wireless connection is a secondary means, more emphasis is on the ribbon connecting means. With the fiber optic ribbon connecting means, a more timely sequence of events is preprogrammed, so that when any of the sensors senses weapons of mass destruction, plurality reaction is enabled through the receptor's random analyzing circuit 244, providng a random detection output through the receptor 110.

The receptor's antenna constantly receives and transmits energy. This transmitted energy powers a circuit responsible for converting alternating current "AC" into direct current "DC." The impedances of the antenna would match the impedances of the circuit. The operating frequency of the receptor 110 is operatively configured with the silicon battery cell 808, The silicon battery cell is configured with a wind energy source configured for wirelessly empowering the receptor 110. The transmitter for the wind energy source sends signals at set frequencies to the circuit board of the receptor 110. The receptor then converts the received signals into DC voltage to charge the receptor. Signal is generated and fed into an amplifier responsive to output signal through a radiating antenna configured to interface with the air. The antenna may be internal, embedded into the circuit board in communication with signal amplifier. The antenna is operatively connected to the amplifier, which is configured with a radio frequency source comprising a circuit that outputs signals to the receptor specified frequency and voltage. The circuit is designed so that when AC current/voltage is inputted, it outputs a DC current voltage—AC to DC converter that would rectifies the AC current voltage and elevates the DC current voltage level. A transformer is configured to isolate the input from the output to prevent overload and transient pikes on the input line.

The configuration of the receptor 110 as seen in FIG. 12 comprises an LED being fired each time the sensors 200 or RFID chip 200a sends a pulse or signal. The pulse rate of emission is adjustable through the potentiometer configuration to enable flexibility for random adaptability to other sensing environment. One lead of the LED represents the anode and the other is a cathode. All the anodes may be connected to the resistors R3. A pulse from any of the sensors enables contact at switch S1, which will then provide connections to networks and other security institutions. When S1 is broken, at least one of the LED will stay lighted to indicate active power in the IR system and can be adjusted to higher clock speed. The transmitter 242 and 311 accepts signals from the sensors in the outfit 10, modifies the signals and transmit the signals through waves or beams to the satellite or network stations "Receiver." The beams, which are of infrared light, are translated at the receiving end back into signals that can be easily amplified to understandable and/or readable information and communication data. Reply from the receiver is obtained through the receiving circuitry comprising receivers 243 and 312 of the receptor 110.

For further military combat settings, FIG. 9 is seen a military advanced combat system's technology which employs a battle ship 800 with wind tower 71 positioned in the sea 801. The wind tower 71 has propeller blades 802 which are aeronautically powered by nature's sea wind 803. The wind tower 71 has a tail-vane 806 that enables the tower to rotate with the wind, creating a kinetic energy along its movement. The kinetic energy along the movement of the wind 803 enables the flow sea current 804, which is then stored in cells 805 responsible for energizing the receptors 110 through the receptor's silicon battery cells 808 of FIG. 8 while in combat operations. The empowerment of the receptors 110 with the energy generated by the wind tower 71 is much powerful and will continuously energize the receptor wirelessly for the entire life of the combat. Creating a night-time and day light energizing means that is much stronger, powerful, and dependable than solar energy means. The receptor utilizes the natural form of electrical energy from ocean current through the wind tower 71. Similar towers could be positioned around the country to empower commercial homeland security receptor devices wirelessly.

The wind tower 71 includes an automatic sensing unit 807 configured with a revolving beacon light and/or an antenna. The antenna is further configured with an amplifier means responsible for emitting constant beams of electrical energy to the receptors 110. The amplifier means is further responsive to detections, and empowering the military outfit 10 to enable unique sensing range. When a sensor 200 or 200a senses gases or other objects, the transmitter 311 will generate a radio frequency signal-using antenna 109 as the communication source. The communications is through continuous wave burst with an identification code unique to the type of wave normally generated by biological or chemical gases and explosives. When such wave signals are matched, communication is enabled to promptly protect the vicinity where such signals were matched. The radio frequency signals are sent and received through the antenna system 109 to the receiver 243 and 312, which are comprised of frequency modulators or modems. The modulator 312 outputs modulated signals to the microprocessor chip 140 as seen in FIG. 1, FIG. 3 and FIG. 4. The microprocessor 140 is operatively configured to filter out the signal output to improve signal to noise ratio and compares with the wave pattern of the coded detection agents.

The sensors 200 or 200a operates on many different principles of detection. These principles include, but are not limited to infrared and thin-film detection, piezoelectric crystal and transducer detection, piezoelectric cantilever detection, piezoelectric MEMS detection and the like. The receptor 110 comprises a cell phone 111 and/or a two-way radio 112, which receives output from each of these sensors and output signals indicative of the signals being received as seen in FIG. 8. The algorithm of the techniques of the sensing pattern minimizes the likelihood of any false detection of deadly agents. The output of each of the sensors and detectors are connected to the input of a central processing unit "CPU" 141 comprising a CMOS 142 as seen in FIG. 8.

FIG. 2 is further seen to show a perspective view of an officer 35 wearing such outfit 10a and patrolling an environment 60, responding to a suspicious areas 90 and/or between suspicious vehicles 50. The outfit 10a is operatively configured to detect deadly gases 700 or explosives 600 around such vehicle 50. The officer 35 is wearing such outfit 10a and patrolling around a suspicious person 40. The detection platform is operatively configured with the outfit 10 to enable detection of explosives 600 or gases 700 within a person 40, if said person has any of such explosives 600 in his possession.

The constructions of explosives 600 and deadly gases 700 have recognizable wavelike properties. The detection platform is configured with sensors that have trained behaviors responsive to the detection of the wavelike properties. The detection platform and the receptor are operatively configured for providing the detected information to be transported in data format to a central security monitoring station 70 or network close to the area of detection.

FIG. 6 is seen to depict a perspective embodiment of receptor 110, comprising vibrating means, ringing means, and/or sounding means operable for sounding an alarm when the detection platform senses any weapon of mass destruction. The detection platform is responsive to detection of any weapon that would require activation of the receptor 110. The receptor is further configured with means for enabling wireless communication to the central security monitoring station 70 or network. The receptor 110 and the detection platform on the outfit may comprise GPS technology coded to identify personnel, their base or location. The base could be the airport or an assigned government building being on alert each time communication is enabled to a central security monitoring station 70.

The transmitted data is communicated to these stations wirelessly for urgent responses to the referenced emergency situation within the vicinity of the detection. This could be explosives 600, chemical agent 620, gases 700, biological agent 630 or other agents and the like, which are normally hidden in a transit bus. Disclosed embodiments provide wearable detection outfit for. Certain embodiments provide the sensors in the outfit configured with pattern recognition technique. The outfit further provides discerning meaningful destructive information on detected materials that are mostly carried by people in anticipation of terrorist or destructive intensions. Embodiments provide the outfit communicatively configured with the receptor, comprising significant recognizable pattern technique to enable prompt actions to any emergency situation.

Embodiments further provide H-LIST comprising a detection system, which is comprised of a biological, chemical, or explosive tool. H-LIST enables wireless communications and comprises to receptors 110 configured with a central security monitoring stations 70. Certain embodiments provide apparatus to facilitate the work of TSA, military, police officers, civil establishment hospitals, transit authorities, and home land security, filtering out analyzed data from an environment 60 and communicating the data to a portable receptor 110 configured to relay the communication to the nearest central security monitoring station 70 or network 69.

FIG. 3 is further seen to show H-LIST detection which allows subsequent position readout from cantilever beam deflection technique. The deflection technique comprise of micro-fabricated array of cantilever type sensors 210 embedded in the silicon substrate 205 and etched/fused on the micro-fibered material 220, providing a detection platform on a wearable outfit operable for mobile detection within an environment 60. The cantilever 210 is coated at the side with different sensor material 212 to further provide detection of specific gases 700 or explosives 600. Embodiments provide apparatus operable to detect wavelike patterns for detection types 600 and 700. The sensors are selectively arranged in (a) micro-machined etched cavities 216 on silicon substrate 205 or wafers with the rear face terminated with micro-fibered materials 220 acting as a lining 20 or insulator. The material 220 comprises multifunctional sensors 215 operable to provide multiple detections through knowledge, and information on optical properties of the sensing gases 700 and explosive elements 600 as they are being exposed to the analyte 175 carrying aqueous solutions.

Certain embodiments provide H-LIST detection which operates on multifunctional sensing and further employs an electronic nose 230 to enable detection of different odors from the receptor layers 170 to the analyte 175. The receptor 110 is operatively configured with an analyte chamber 195, which is linked to the silicon substrate sensor array configured with the micro-fibered material 220. The silicon substrate array is interfaced with the output connector 25 of the said micro-fibered fabric 220. The outfit 10 comprises input adaptor 160 configured with the receptor 110, to provide advanced detection selectivity and sensitivity. The receptor is operable to expedite timely responses to multifunctional detections. The array of the cantilever 210 is micro-mechanical, operable with multiple silicon substrate cantilevers that are linked to the analyte chamber 195. The analyte chamber 195 is configured to absorb and analyze sensed information.

Grains of membrane 190 are etched in the analyte chamber 195 as seen in FIG. 3 to enable signal separation for specific reporting to network stations 69. The cantilevers 210 comprises of at least a micro-machined single crystal microcantilevers with multiple resistors. The resistors further comprises piezoresistor 211, being fabricated in the cantilevers 210, and operable for determining the cantilever stresses resulting from stress films deposition on the cantilevers 210. FIG. 3 further shows a capacitor cantilever beam 212 configured to electro-statically be pulled-in into a substrate 205, to enable the pulled-in voltage (Vp) to operate as a function of the dimensions of the micro-beam devices 280 and the modulus and stress state of the beams 280. The beam deflection signals are transformed into information specific to the analytical useful signal from the reaction of the analyte 175 or the physical property of the investigative agent 176. The analyzed information is communicable simultaneously through a beam deflection 284, outputting through a multifunctional fiber-optic ribbon 240 and/or micro electronic grains of sensors.

Multiple light sources 245 are connected through the membrane 190 into the analyte chamber 195 to illuminate individual cantilever 210 with light beam through the fiber. The deflection of the light 245 from the cantilevers 210 is configured to shine on a position sensitive detector 250. The position sensitive detector 250 enables bending of related sensors through photocurrent 275 due to stress factor acting on the beam 280. The photocurrent 275 is then transformed into voltage (Vp) and the voltage creates pressure on the cantilever 210, enabling bending indicative of the detected signals being communicated to the central security monitoring/communication station 70. The occurrence of the bending is due to surface stress on the sensors and creates resonance frequency shift 514 caused by the surface stress change, which is subsequently caused by the change of mass 265 as seen in FIG. 1, FIG. 3, and FIG. 4.

FIG. 4 is seen to show a piezoelectric micro-mechanical system and thin film in the detection system. Embodiments provide the detection platform comprising a combination of micro-electro-mechanical systems 420 and thin film 430 technologies into the design of H-LIST detection. The H-LIST detection include the integration of silicon micro-fibered materials 220 and microelectronics circuits 410 into multifunctional sensor arrays 330. The sensor array 330 is fabricated on a sensor in silicon substrates 205 to provide further sensitivity. The sensor array may be affixed on at least a material for the outfit fabric the detection platform. The detection platform is configured for detecting biological, chemical, mechanical, and physical parameters of enforceable destructive material/agent. The thin film and the micro-electro-mechanical process requires the sensors to be embedded inside the silicon substrate 205 and etched inside the micro-fibered material 220 or other fabric materials. The microelectronic circuit 410 is further integrated into the detection platform for the H-LIST device and interfaced with multiple sensors. The designed patterns of the sensors are responsible for advancing pattern recognition techniques through the application of the sensing materials being used for the development of the detection platform.

Disclosed embodiments further provide application and implementation of H-LIST, which prescribes advanced sensors for multifunctional applications and the integration of other technologies to enhance interactive homeland security detection system by adopting other microprocessor electronics 85 as seen in FIG. 6 into a digitized system. The microprocessor electronics 85 is further responsive to wireless/mobile detections of biochemical, chemical agents, providing multifunctional sensing through a wearable fashioned outfit 10a. The outfit is worn by law enforcers, or security officers 35, or other government agencies for monitoring biological and chemical gases 700 or other explosive elements within a common environment 60 or for national security and global protection.

H-LIST could be transformed into H-LIST.IP Homeland Intelligence systems Technology for International Protection," and will search and process any material of mass destruction such as biological, chemical gas, or other explosive devices in an assigned environment. Disclosed embodiments provide detection platform comprising tiny grains of the sensors 200 and 200a being embedded in a silicon substrate 205 and affixed on a micro-fibered material 220. The micro-fibered material 220 is affixed on the interior of a regular outfit 10a, such that are normally worn by officers, security officers 35, law enforcement officers, military personnel, Doctors, civil establishment hospital patients and the like as seen in FIG. 15. The tiny grains of sensors comprise of nano-sensors 200 being trained to recognize different gases 700, biological 630, chemical 620, or explosive materials in their wavelike pattern structure. The sensors are intelligently constructed and architecturally structured to invisibly run through the silicon substrate 205 in the micro-fibered material 220. The sensors comprises nanotechnology applications consisting of tiny grains of sensors 200 or 200a being coded and wired in the micro-fibered material 220, such that an extended output connector 25 is exposed out of the micro-fibered material 220 to the side of the outer or inner assembly of the wearable outfit 10a.

Disclosed embodiment further provide a rechargeable receptor 110 being worn on a waist belt 120 and on the waist area 130 of the security officer 35 as seen in FIG. 13. The receptor 110 comprises an input terminal comprising adaptor 160 in communication with the detection platform being communicatively connected to the receptor 110.

FIG. 5 is seen to show a receptor 110 and a detection platform on the outfit 10a worn on the officer's body to further detect personnel's physiological conditions. A silicon micro-fibered material 220 is affixed on the detection platform for the outfit 10. The affixation in certain embodiment, could be easily detached off the outfit 10 during normal cleaning. The silicon micro-fibered material 220 acts as an insulator on the officer's body, and further comprise of detectors on its mobile environment 60. The outfit is responsive to intelligent monitoring of explosives 700 or deadly devices. The sensors 200 and 200a run through the interior part of the outfit 10a, and the output terminal 25 extends outwardly at the lower side of the outfit 10a, such that the extended output connector 25 is connected to the input adaptor 160 of the receptor 110. The receptor 110 is made of microelectronic materials comprising intelligent microprocessor chip 140 that empowers the trained brains of the embedded sensors 200 or 200a being disposed in the silicon micro-fibered material 220. The sensors are responsible for timely detections of deadly materials or weapons of mass destructions and the receptor's analysis and reporting is seamlessly in real time.

The receptor 110 connects and report to the central security monitoring station 70 through wireless networks 66 or wind towers 71 and remotely empowers the detection platform, enabling it to monitor assigned environments 60 for materials such as radioactive cesium, chemical, biological, explosives, toxic, biochemical, and the like. Such an environment 60 includes, but is not limited to battlefield, office buildings, public recreation areas, transportation equipment, city centers, stadiums, government buildings, airports, schools, tunnels, civil establishment hospitals and the like. The application of H-LIST further advances the knowledge needed in monitoring anticipatory or suspected terrorist(s) acts and also enables Homeland Intelligence Systems to be more communicative by advancing knowledge and information systems into a detection platform. The detection platform further contain information of suspected terrorist movements via the receptor. The application of H-LIST is further integrated in either analog or digital systems or both, with higher degree of processing of large information at much higher sensing speed. Disclosed embodiments provide advanced sensing through the multifunctional sensors 215. Detections and communications are provided simultaneously with higher communication signal strength to noise ratio. The multifunctional sensors 215 are further responsive to cross sensitivity being covered by the sensing amplification through the receptor chips 140. The detection platform 295, which consist of sensors, is operatively configured with detectors 290 and responsive to communications through an active interface means with variable electrical, mechanical, optical, or chemical impedance. The detection platform 295 further generates electrical output signals or pulses indicative of the detected information and enables communication thereof.

As further shown in FIG. 6, sensors 200 and 200a are developed with optimized selectivity and sensitivity, using semiconductor fabrication line in their development process to enable communication of human body responses to at least an environment, such as physiological conditions of personnel, including heart rates or respiratory data reporting. Because of the selectivity and sensitivity of explosive 600 and other chemical or biochemical materials, different materials being provided, nanocrystalline material could be used in patterning the sensing medium. These materials offer immersed promises to improving the sensitivity of H-LIST detection. In targeting mixed gases and some odors within a confined environment, other devices such as electronic nose 230 are used to detect specific patterns or finger prints of the gas mixtures, which may consist of more than one chemical sensors to sense a specific gas and also be trained for a particular pattern recognition via a system in detecting explosives 600 and other destructive materials. The incorporation of a detection platform 295 on outfit 10a for sensing and detecting of weapons of mass destruction further embraces multiple sensors for mobile detection. In similar configurations, a silicon micro-fibered multifunctional-sensor array 330, gas sensing and other sensing are seen responsive to changes in the surface or near surface oxide conductivity 440, which are caused by the formation of space charge region 445 induced by gas absorption or oxygen vacancies on the surface environment 446.

Discloses embodiments further provide detection of gas concentration as seen in FIG. 4. Gas selectivity, which is the detection of specific gases 700 in a mixed gas environment 60, is very importance in the smartness of the disclosure. Disclosed embodiments provide silicon micro-fibered material 220 and the fabrication of microelectronic circuit 410 as shown in FIG. 6 to enhance H-LIST detection. Certain embodiments provide a silicon substrate 205 being micromachined through a chemical or electrochemical etch technique, employing silicon-to-silicon 460 and or silicon-to-glass and or ceramic wafer bonding 470. This bonding is responsive to strengthen the micro machining or microelectronics integration to enable multifunctional sensing 215. The silicon-to-glass and or ceramic wafer bonding 470 is seen in FIG. 4 to allow the use of single crystal silicon instead of polycrystalline silicon to improve the design of micro-acoustics and micro optics and also to provide an energy platform for converting solar energy, sound wave, vibration, pressure force, and wind force into electrical energy. The micro-acoustics and micro-optics are further fabricated in the micro-electro-mechanical system 420 and thin film technique 430 to enable the integration of microelectronics circuit 410 and multifunctional sensor 215 into the detection platform 295 on the outfit 10a. Wafer bonding 460 and 470 in single crystal silicon would significantly lower acoustic losses and improve optical properties and energy production.

Though other bonding method may be used in the microelectronic processes, the detection platform is configured with sensitive electronic being operable for monitoring comprises the MEMS 420 and piezoelectric sensors 180 shown in FIG. 4 and FIG. 6 or the cantilever sensor 210 shown in FIG. 3 and FIG. 1 operable for wearable outfit 10, 10A, 20, 30 and 120. With these, bulk and surface acoustic wave resonators 500 are configured for multifunctional, physical, and chemical sensing, and includes other sensors like viscosity sensors and the like as seen in FIG. 4. The resonator-based sensor 500 measures resonance frequency shift such as in surface plasmun resonance spectroscope, caused by mechanical, chemical, or electrical perturbation of the boundary conditions on the active interface 300. These electrical perturbations occur in metal films 543 with different conductivity values deposited on the resonator 500, enabling various loading effects in the liquid and solid media 505, which will damp the oscillations 514 of the resonator 500 and modify the sensor resolution.

The resolution of the sensor is determined by the resonance frequency shift response to the external perturbations, adding the capacity of the monitoring electronics to accurately measure the frequency shift within the detection environment and enabling damping of the oscillation 514. The damping of the oscillating frequency is caused by the acoustic energy drained which occurs when free quartz resonance 510 is brought to contact with solid liquid medium 505.

Disclosed embodiments provide resonators such as mechanical resonators 500 to measure the frequencies and to provide higher accuracy in sensor sensitivity and selectivity.

However, the selectivity process depend on the parameters of the gas absorption and co-absorption mechanism, surface reaction kinetics, and electron transfer to and from the conduction band of the semiconductor 142, which are achieved by enhancing gas absorption or electronic effect in plurality method such as surface modification. The enhancement can also be influenced by the addition of metal clusters 520 to increase the sensor sensitivity caused by close coupling between the sensing 400 and catalytic properties 504 of the metal oxide 530.

FIG. 4 further shows metal clusters 520, which are added to the sensors 180, 200a and 200 to increase selectivity and consist of chemical sensitization, which enables metal particles 522 acting as centers for surface-gas absorption and may spill over onto the oxide surface 540, providing reaction with the negatively charged chemisorbed oxygen. The addition of metal clusters 520 enables electronic sensitization resulting from (a) direct electronic interaction between the oxide surface 540 and the metal particles 522 through metal oxidation and reduction processes.

In other embodiment, thin film coating 430, which is sensitive to the measured parameters of the sensors, is deposited on the resonator 500 to enable changes in the physical or chemical parameters that will change the resonant frequency shift. The resonant-based sensors 180 and 200 are configured to measure resonant frequencies shifts caused by mechanical, electrical perturbations, chemical or biochemical equivalent. With the incorporation of piezoelectric resonator 500, electrical perturbation will occur in the metal films 543 with different conductivity values deposited on the resonator. When the resonator 500 is immersed in water, it will be deposited in ion-conducting electrolyte. The resolution of the sensors is determined by the resonance frequency shift in response to the external perturbations and the capacity of the monitoring electronics to accurately measure the frequencies. Disclosed embodiments provide amplification of electronic signals through multifunctional sensors 215. In this, the oxidized particles are reduced, providing a change in carrier concentration of the semiconductor oxide substrate 560 to enhance sensitivity through doping to modify the carrier concentration and mobility, or through micro structured changes by the reduction of oxide particle sizes.

Certain embodiments provide film processing comprising thin film deposition processes like chemical vapor condensation or sputtering, and screen-printing or tape casting. Embodiments provide the thin film 430 being deposited on the piezoelectric resonant line 570, providing additional acoustic shear wave modes that will not couple electrically to fluid to avoid heavy loss of acoustic energy. Each film is provided to detect a corresponding gas component. Still in other embodiment, silicon and a non-piezoelectric substrate are used to configure a surface acoustical wave to enable detection selectivity and sensitivity. Some embodiments provide transducers 315 being coated with ZnO, which is a piezoelectric material that is deposited using reactive magnetron sputtering. The surface acoustic wave line 570 is enabled when the sensing coating changes its mechanical parameters in the presence of the gas to which partial pressure is measured, providing the resonant frequency shifts due to the surface acoustic wave propagation velocity. The surface acoustic wave line 570 is coated with passive glass film for calibration, allowing the pattern recognition techniques to be administered and detection data are communicated in order to analyze the signals coming from the various sensor arrays 330. The resonator 500 has a maximum conductivity and behaves like a resistor corresponding to a zero phase shift.

In another embodiment of the instant invention, FIG. 9 is seen a military ship 800 positioned in the sea 801. The sea 801 comprises wind current 804 traveling through waves 820, such as radio wave or microwaves being empowered by a wind energy source 830. The operation of the wind energy source 830 is interactive with at least a turbine 840 responsive to ocean current for generating matching electrical energy in communication with apparatus to detect weapons of mass destruction. Such weapons of mass destruction include verbal aerial communication between enemy networks such as networks run by terrorist groups. The wind energy source 830 communicatively connected to wind fiber tower 71 to enable interactive networks spectrum for communication indicative of reaching homeland security broadband networks for local, state, regional and federal first responders. Whereby the outfit comprises a platform for detection and is configured with a receptor for providing high resolution chemical, biological and explosive detection data and other critical data to first responders.

In another embodiment, FIG. 4 is further seen a paste or ink 585 printed on a suitable substrate with two-stage heat treatment to form a dense layer with a favorable structure. In yet another embodiment, the paste 585, which is of powder mixed with an organic medium and a binder, collaborate the correct theological properties to deposit layers of sensor materials on the substrate.

The paste 585 further contains nanoparticles, being deposited in different substrates and heated at various temperatures to obtain the required dimension of the film 430, providing reactive sputtering processes or vapor deposition process that is superior for the use of H-LIST wearable outfit in mobile detection, monitoring and security. Still in another embodiment, a low temperature and pressure deposited aluminum Nitride "AlN" thin film 316 is used to integrate with microelectronic devices and sensors with conventional photolithographic patterning technique, being embedded in a silicon substrate 205, and etched on a micro-fibered fabric material 220 for the outfit 10a. Other materials that are not mentioned in the perspective embodiment could be used as a fabric to etch the embedded sensor on the silicon substrate 205. A flexural plate wave gravimeter sensor fabricated from SOI wafers will enable the aluminum nitride "AlN" 316 to be deposited on its surface, allowing the integrated digital transducers 315 to act on the piezoelectric aluminum nitride layer to enable the lunching and detection of plate waves on a thin silicon membrane 190, which is coated with binding site-specific polymers, such that a change in the silicon membrane resonance frequency will detect a change in the piezoelectric crystal mass 265 as a result of a subsequent change in the membrane mass 195. Disclosed embodiments provide an energy platform comprising SOI wafers.

The binding of the associated antibody/antigen caused by specific recognition will result in mass increase and decrease in frequency. The change of frequency reflects the presence and amount of the targets. In another embodiment, the piezoelectric AlN thin film is deposited on a glass and or ceramic substrates and embedded in a silicon material to improve the flexibility of the sensors 180, 200, and 200a etched in the micro-fibered material 220, allowing specific designs that are prescribed for any outfit for enabling detection of personnel's physiological conditions and for security monitoring of deadly gases 700 and explosives 600. Certain embodiments provide an energy platform comprising AlN thin film. Achievement is obtained through manipulation of the structure of the film by controlling the deposition parameter precisely. However, both nanopowder and nanostructured film are utilized in some disclosure. Nanostructured materials are the essentials to achieving high gas sensitivity, but the technique requires desired oxide composition with a specific dopant and few processing steps. Oxide materials are made more sensitive by introducing dopants, which have unique gas absorption characteristics and utilizes materials with specific catalytic properties to enhance gas sensitivity.

The drawings clearly outline the scope and embodiment of disclosed embodiments. As per FIG. 12, the following components are further explained.
1C1=CPU
1C2=RFID Chip reader
L1+L2=LED
S1=ASPDT "Automatic momentary single pole double throw" switch, for transmitting and receiving signals.
CI=Electrolytic capacitor
C2=imf capacitor
C3=imf capacitor
Q1=Infrared or general purpose silicon transistor
Q2=Phototransistor detector
L1=Infrared LED emitter
M1=speaker/microphone
R1 through R10=Resistors While certain aspects and embodiments of the disclosure have been described, these have been presented by way of example only, and are not intended to limit the scope of the disclosure.

Indeed, the novel of the apparatus described herein may be embodied in a variety of other forms without departing from the spirit thereof. The accompanying claims and their equivalents are intended to cover such forms or modifications as would fall within the scope and spirit of the disclosure. It is to be understood that the scope of the present invention is not limited to the above description, but encompasses the following claims:

What is claimed:

1. A wearable apparatus configured for effective detection selectivity and for monitoring contextual characteristics influential to environmental change, the apparatus is further configured for providing advanced intelligence and security monitoring; comprising:
   a plurality of sensors embedded in at least a silicon substrate and etched/fused in at least a micro-fibered material to provide effective detection platform, said detection platform configured to detect pre-use and/or post use of deadly weapons in at least a monitoring environment; and
   at least a wireless communication apparatus in communication with said detection platform for analyzing detection signal and enabling wireless communications to at least a remote monitoring apparatus, wherein said remote monitoring apparatus includes a control center/command post, a transmitter, and a receiver;

said detection platform further configured to convert at least one of solar energy, wind, sound wave, vibration and/or force/pressure into electrical energy to power itself, said micro-fibered material further configured with at least an alloyed material comprising at least miniaturized steels for providing protection against at least bullet penetration.

2. A wearable apparatus of claim 1, wherein said communication apparatus further comprising at least a transmitter apparatus communicatively connected to said detection platform.

3. A wearable apparatus of claim 1, wherein said communication apparatus is communicatively configured for providing at least interactive communications.

4. A wearable apparatus of claim 1, wherein said sensor apparatus is embedded/fused in at least a silicon substrate.

5. A wearable apparatus of claim 1, wherein said silicon substrate is embedded/fused in at least a micro-fibered material, and said micro fibered material further comprising at least a material with excellent electrical properties.

6. A wearable apparatus of claim 1, wherein said detection platform further comprises said silicon substrate being disposed with said micro-fibered material, wherein said detection platform operatively configured for thermal control, and wherein said micro-fibered material further providing effective and/or efficient communications clarity and detection sensitivity.

7. A wearable apparatus of claim 1, wherein said detection platform further configured for detecting concealed weapons.

8. A wearable apparatus of claim 1, wherein said detection platform further comprises at least a nanotechnology applications.

9. A wearable apparatus of claim 1, wherein said sensor apparatus comprises nanotechnology applications; further comprises at least nano-sensors.

10. A wearable apparatus of claim 1, wherein said sensor apparatus further include at least one of: a MEMS, silicon metal oxides, GPS, thin film, piezoelectric, cantilever, and membrane.

11. A wearable apparatus of claim 1, wherein the communication apparatus is communicatively connected to said detection platform, said communication apparatus further being responsive to communication signals from said detection platform, wherein said communication signals is indicative of detection of at least one of weapons of mass destruction, concealed weapons, alcohol, drugs, energy, sounds, waves, perspiration, physiological change, and medical conditions.

12. A wearable apparatus of claim 1, wherein the communication apparatus operatively configured with said detection platform for converting detection signals into useful communicable analytical signals.

13. A wearable apparatus of claim 1, wherein the communication apparatus is further configured with said detection platform for analyzing detection signals of varying frequencies.

14. A wearable apparatus of claim 1, wherein the detection platform further comprising means for detecting weapons of mass destruction.

15. A wearable apparatus of claim 1, wherein the detection platform further comprising means for detecting at least concealed weapons.

16. A wearable apparatus of claim 1, wherein the detection platform further comprising means for detecting physiological conditions, and wherein said physiological conditions further comprising at least a heart rate and/or at least a vital signs.

17. A wearable apparatus of claim 1, wherein said detection platform further comprising means for detecting at least one of: a biological agent; chemical agent; personnel position, vital signs, enemy position, pre-used and/or post-used of at least a weapon, and radiological agent.

18. A wearable apparatus of claim 1, wherein said detection platform further configured for converting at least one of: solar energy, wind, sound wave, vibration and/or force/pressure into electrical energy.

19. A wearable apparatus of claim 1, wherein the miniaturized steel further comprising at least zinc oxide (ZnO), wherein the detection platform further configured with at least one of: polymers, glass substrate, ceramic substrate, nonwoven material, nanostructure materials, and/or materials with absorption characteristics, and wherein said communication apparatus responsive to at least a detection and/or said electrical energy.

20. A wearable apparatus of claim 1, wherein the detection platform further responsive to at least civil establishment hospitals applications.

21. A wearable apparatus of claim 1, wherein the detection platform further responsive to at least sport personnel applications.

22. A wearable apparatus of claim 1, wherein the detection platform is being worn by at least a person to provide for environmental protection and/or environmental detection.

23. A wearable apparatus of claim 1, wherein the detection platform further configured for communicating/administering at least a patient medical conditions/treatment.

24. A wearable apparatus of claim 1, wherein the detection platform further responsive to environmental conditions, further comprises means for providing thermal adjustment to at least the conditions and/or situations of at least a personnel/environment.

25. A wearable apparatus of claim 1, wherein the detection platform further comprises force responsive apparatus being operable for providing body protection against at least environmental conditions.

26. A wearable apparatus of claim 1, wherein the sensor apparatus further comprises discrete regions comprising membranes configured for analyzing data.

27. A wearable apparatus of claim 26, wherein said discrete regions further configured with the communication apparatus, further comprising at least a cleansing of the affinity column for extracting at least an analyte of dissolved and/or suspended material other than the bound analyte.

28. A wearable apparatus of claim 27, wherein said discrete regions further responsive to at least a releasing of the analyte from the affinity column, said communication apparatus further providing the analyte with a measurable fluorescence when the analyte does not have a measurable natural fluorescence, said discrete region further comprises at least a reflecting layer for enhancing detection sensitivity.

29. A wearable apparatus of claim 1, wherein said detection platform further comprises at least a military outfit.

30. A wearable apparatus of claim 1, wherein said detection platform further comprises at least a pathogen detector being further operable for destroying at least a bacteria.

31. A wearable apparatus of claim 1, wherein said detection platform further configured for amplifying at least a DNA for a destroyed bacteria, further comprising apparatus for detecting at least a specific pathogen.

32. A wearable apparatus of claim 1, wherein the detection platform further configured for at least nuclear agent detection.

33. A wearable apparatus of claim 1, wherein said detection platform further responsive to change in physiological conditions, further operable for detecting/monitoring medical conditions.

34. A wearable apparatus of claim 1, wherein said detection platform further configured for administrating medication/treatment to at least a person.

35. A wearable apparatus of claim 1, wherein said detection platform further configured for detecting bleeding, and wherein said detection platform being configured for administering at least a treatment to said bleeding portion of the body.

36. A wearable apparatus of claim 35, further comprises at least a tourniquet apparatus.

37. A wearable apparatus of claim 1, wherein said detection platform further responsive to at least one of: the conditions, location, and situation of at least a personnel, and wherein said sensor apparatus further comprises at least a global positioning system.

38. A wearable apparatus of claim 1, wherein said communication apparatus further configured for obtaining updated commands, further comprising receiving at least information regarding the environmental exposure to weapons of mass destructions, including at least one of biological, chemical, radiological, and nuclear agents.

39. A wearable apparatus of claim 1, wherein said detection platform further configured for analyzing at least a DNA sample for identifying at least an enemy wearing the same outfit taking from at least a downed personnel.

40. A wearable apparatus of claim 1, wherein said detection platform further configured for analyzing at least odors.

41. A wearable apparatus of claim 1, wherein said detection platform further comprises at least a material comprising at least one of: silicon substrate, nonwoven material, miniaturized steels, miniaturized alloyed material, and/or micro fiber material.

42. A wearable apparatus of claim 1, wherein said detection platform configured with said sensor apparatus and embedded/fused in said at least one material.

43. A wearable apparatus of claim 1, wherein said detection platform configured with said communication apparatus, further comprising alcohol monitoring apparatus.

44. A wearable apparatus of claim 1, wherein said communication apparatus further comprises web based applications, further comprising means for monitoring juvenile offenders.

45. A wearable apparatus of claim 1, further comprises continuous remote monitoring apparatus.

46. A wearable apparatus of claim 1, further comprises mobile electronic monitoring apparatus.

47. A wearable apparatus of claim 1, wherein said detection platform further comprises at least one of: an anklets; a bracelet; and a neck let.

48. A wearable apparatus of claim 1, wherein said detection platform further comprises at least a fuel cell.

49. A wearable apparatus of claim 1, wherein said communication apparatus further comprises at least one of: a modem, and a browser, a portable device, a transportable device, a mobile device, and/or an analyzer, further comprises means for sampling perspiration.

* * * * *

UNITED STATES PATENT AND TRADEMARK OFFICE
CERTIFICATE OF CORRECTION

| | |
|---|---|
| PATENT NO. | : 7,872,575 B2 |
| APPLICATION NO. | : 11/821776 |
| DATED | : January 18, 2011 |
| INVENTOR(S) | : Tabe |

It is certified that error appears in the above-identified patent and that said Letters Patent is hereby corrected as shown below:

Delete Drawing sheet 11 of 18 and insert Drawing sheet 11 as attached.

Signed and Sealed this
Thirtieth Day of August, 2011

David J. Kappos
*Director of the United States Patent and Trademark Office*